(12) United States Patent
Grenz et al.

(10) Patent No.: US 11,129,994 B2
(45) Date of Patent: Sep. 28, 2021

(54) SENSOR-BASED PHRENIC NERVE STIMULATION DETECTION

(71) Applicant: Medtronic, Inc., Minneapolis, MN (US)

(72) Inventors: Nathan A. Grenz, North Oaks, MN (US); Karen J. Kleckner, Blaine, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 16/213,539

(22) Filed: Dec. 7, 2018

(65) Prior Publication Data

US 2019/0175918 A1   Jun. 13, 2019

Related U.S. Application Data

(60) Provisional application No. 62/595,854, filed on Dec. 7, 2017.

(51) Int. Cl.

| *A61N 1/37* | (2006.01) |
| *A61B 5/00* | (2006.01) |
| *A61B 7/04* | (2006.01) |
| *A61B 5/024* | (2006.01) |
| *A61B 7/00* | (2006.01) |
| *A61N 1/365* | (2006.01) |

(Continued)

(52) U.S. Cl.
CPC .......... *A61N 1/3704* (2013.01); *A61B 5/0031* (2013.01); *A61B 5/024* (2013.01); *A61B 5/4029* (2013.01); *A61B 5/7217* (2013.01); *A61B 7/005* (2013.01); *A61B 7/006* (2013.01); *A61B 7/04* (2013.01); *A61N 1/36578* (2013.01); *A61N 1/3702* (2013.01); *A61N 1/37241* (2013.01); *A61N 1/37258* (2013.01); *A61N 1/3627* (2013.01); *A61N 1/36135* (2013.01); *A61N 1/37282* (2013.01)

(58) Field of Classification Search
CPC .... A61N 1/3704; A61B 5/0031; A61B 5/024; A61B 5/4029; A61B 5/7217
See application file for complete search history.

(56) References Cited

U.S. PATENT DOCUMENTS

| 5,117,824 A | 6/1992 | Keimel et al. |
| 7,115,096 B2 | 10/2006 | Siejko et al. |

(Continued)

OTHER PUBLICATIONS

Crossley et al., "Performance of a novel left ventricular lead with short bipolar spacing for cardiac resynchronization therapy: Primary results of the Attain Performa Quadripolar Left Ventricular Lead Study," *Heart Rhythm Society*, Apr. 2015; 12(4):751-8.

(Continued)

*Primary Examiner* — Joseph M Dietrich
(74) *Attorney, Agent, or Firm* — Mueting Raasch Group

(57) ABSTRACT

A method and device for detecting phrenic nerve stimulation (PNS) in, or using, a cardiac medical device. A test signal sensitive to contraction of a diaphragm of a patient may be sensed and signal artifacts of the test signal within each of a first window of the test signal prior to a predetermined cardiac signal and a second window of the test signal subsequent to the predetermined cardiac signal may be determined. The PNS beat criteria may be evaluated, for example, using the test signal, which may be a heart sounds signal.

23 Claims, 10 Drawing Sheets

(51) Int. Cl.
    *A61N 1/372*     (2006.01)
    *A61N 1/362*     (2006.01)
    *A61N 1/36*     (2006.01)

(56) References Cited

U.S. PATENT DOCUMENTS

| | | |
|---|---|---|
| 8,527,051 B1 | 9/2013 | Hedberg et al. |
| 8,532,774 B1 | 9/2013 | Hedberg et al. |
| 9,421,383 B2 | 8/2016 | Rockweiler et al. |
| 9,649,498 B2 | 5/2017 | Mahajan et al. |
| 2012/0296388 A1 | 11/2012 | Zhang et al. |
| 2013/0289640 A1 | 10/2013 | Zhang et al. |
| 2015/0265840 A1 | 9/2015 | Ghosh et al. |

OTHER PUBLICATIONS

Schapira et al., "Relation of P-S4 interval to left ventricular end-diastolic pressure," *Br Heart J.*, Mar. 1982; 47(3):270-6.
International Search Report and Written Opinion for International Application No. PCT/US2018/064509, dated Mar. 18, 2019, 16 pages.

SENSOR-BASED PHRENIC NERVE STIMULATION DETECTION

This application claims the benefit of U.S. Provisional Patent Application Ser. No. 62/595,854 filed on Dec. 7, 2017, which is incorporated by reference in its entirety.

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. The implantable medical leads may be configured to allow one or more electrodes and/or sensors to be positioned at desired locations for sensing and/or delivery of stimulation. For example, electrodes or sensors are positioned at a distal portion of the lead and a connector is positioned at a proximal portion of the lead and coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device senses for intrinsic depolarizations of the heart, and controls the delivery of such signals to the heart based on the sensing. Upon detection of an abnormal rhythm, such as bradycardia, tachycardia or fibrillation, for example, an appropriate electrical signal or signals may be delivered to restore the normal rhythm. For example, in some cases, an implantable medical device delivers pacing, cardioversion, or defibrillation signals to the heart of the patient upon detecting ventricular tachycardia, and delivers defibrillation electrical signals to a patient's heart upon detecting ventricular fibrillation. Pacing signals typically have a lower energy than the cardioversion or defibrillation signals.

Pacing signals, cardioversion signals and defibrillation signals may affect tissue and nerves outside of the target tissue. For example, a pacing pulse applied to the left ventricle may also result in unintended phrenic nerve stimulation (PNS). In other examples, an electrical lead may be placed proximate to the phrenic nerve and provide stimulation designed to stimulate the phrenic nerve. During cardiac stimulation, PNS may cause unpleasant side effects for a patient, such as hiccups, dyspnea, uncomfortable muscle twitching and general malaise. PNS may also decrease the hemodynamic response to cardiac resynchronization therapy (CRT), or generally impair the hemodynamic performance of the heart, in the patient. When implanting a pacemaker, including lead placement, and setting pacing parameters (e.g., choosing the strength of stimulus), a physician or other clinician may attempt to detect and avoid PNS. In other instances, PNS may be provided as an additional therapy option for certain patients with a respiratory disorder.

Phrenic nerve stimulation (PNS) during left ventricular (LV) pacing for cardiac resynchronization therapy (CRT) may occur when the electrodes are near the phrenic nerve, leading to contraction of the diaphragm and patient discomfort. The development of quadripolar LV leads has reduced the rate of PNS complications requiring invasive LV lead repositioning or discontinuation of CRT, but PNS is still commonly encountered during implant and at patient follow-up, requiring either surgical intervention or reprogramming to resolve.

SUMMARY

In general, the disclosure is directed to detection of phrenic nerve stimulation (PNS) using a heart sounds sensor in a cardiac medical device. In some examples, pacing-induced phrenic nerve stimulation is detected using the techniques described herein. In some examples, asymptomatic phrenic nerve stimulation is detected. In some examples, intentional, e.g., therapeutic, PNS is detected using the techniques described herein, e.g., to evaluate whether PNS has been achieved or the efficacy of PNS.

In one example, the disclosure is directed to a method of detecting phrenic nerve stimulation (PNS) in a cardiac medical device that includes sensing a test signal, the test signal being sensitive to contraction of a diaphragm of a patient; determining signal artifacts of the test signal within each of a first window of the test signal prior to a predetermined cardiac signal and a second window of the test signal subsequent to the predetermined cardiac signal; determining, in response to signal artifacts of the test signal within the first window and the second window, whether PNS beat criteria have been satisfied; determining, in response to the PNS beat criteria being satisfied, whether PNS episode criteria have been satisfied; and detecting a PNS episode in response to the PNS episode criteria being satisfied.

In another example, the disclosure is directed to a cardiac medical device, comprising: a first sensor configured to sense a test signal, the test signal being sensitive to contraction of a diaphragm of a patient; a second sensor to a predetermined cardiac signal; and a processor configured to determine signal artifacts of the test signal within each of a first window of the test signal prior to a predetermined cardiac signal and a second window of the test signal subsequent to the predetermined cardiac signal, determine, in response to signal artifacts of the test signal within the first window and the second window, whether PNS beat criteria have been satisfied, determine, in response to the PNS beat criteria being satisfied, whether PNS episode criteria have been satisfied, and detect.

In another example, the disclosure is directed to a non-transitory computer readable medium storing instructions which cause a cardiac medical device to perform a method comprising: sensing a test signal, the test signal being sensitive to contraction of a diaphragm of a patient; determining signal artifacts of the test signal within each of a first window of the test signal prior to a predetermined cardiac signal and a second window of the test signal subsequent to the predetermined cardiac signal; determining, in response to signal artifacts of the test signal within the first window and the second window, whether PNS beat criteria have been satisfied; determining, in response to the PNS beat criteria being satisfied, whether PNS episode criteria have been satisfied; and detecting a PNS episode in response to the PNS episode criteria being satisfied.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
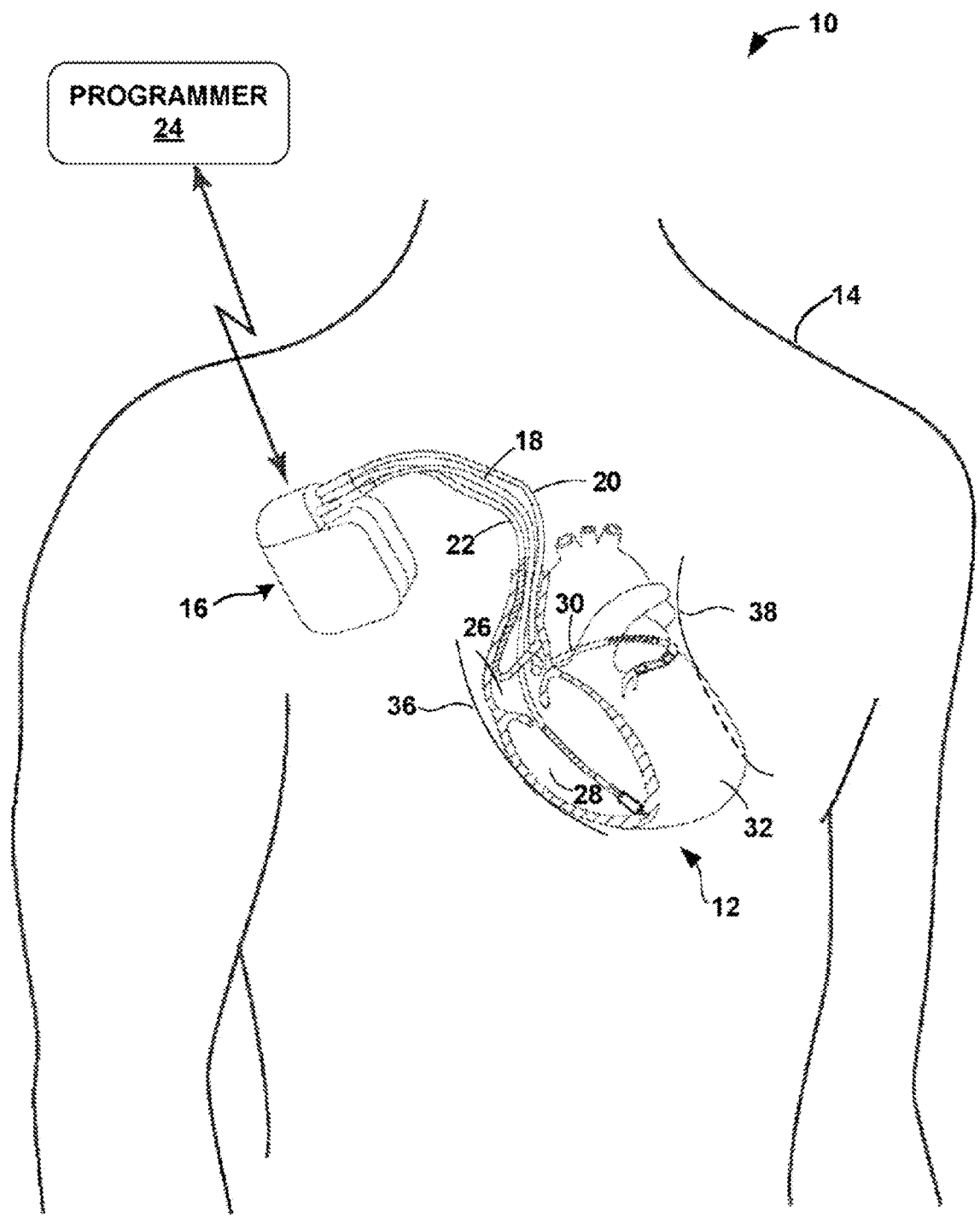
FIG. 1 is a conceptual diagram illustrating an example system that detects phrenic nerve stimulation, consistent with an example of the present disclosure.

The techniques described in this disclosure may allow a medical device to automatically detect the presence of phrenic nerve stimulation. In some examples, the phrenic nerve stimulation is an unintended side effect of electrical stimulation applied to a patient's heart. In other examples, the detected phrenic nerve stimulation may be purposeful. For example, phrenic nerve stimulation may be used to treat neurological disorders affecting mechanical ventilation. In various examples, the detection of phrenic nerve stimulation occurs in response to an activation event. The activation event may be a change in the electrical stimulation applied to the patient's heart. In other examples, the activation event may be a posture or activity level of the patient detected by a posture or activity sensor. For example, an activation event may be an indication that the patient is lying down. In other examples, the activation event may be the detection of low activity of the patient. In some examples, the activation event may be the detection of combination of factors. For example, an activation event may be on the occurrence of a particular posture or activity in conjunction with a change in the electrical stimulation. In other examples, the activation event may be based on time. For example, an activation event may be the passage of predetermined amount of time since the previous phrenic nerve detection sequence. In still other examples, the activation event may be on the occurrence of a particular time of day. In another example, the detection of phrenic nerve stimulation may be initiated through input at a user interface of a device external to the medical device, such as during implant of the medical device, post-implant, or during an office follow-up visit by the patient either remotely or in office, for example. In another example, the medical device may continuously and ambulatorily analyze heart sounds signals for detection of phrenic nerve without the use of an activation event.

Heart sounds are associated with mechanical vibrations from activity of a patient's heart and the flow of blood through the heart. Heart sounds recur with each cardiac cycle and are separated and classified according to the activity associated with the vibration. As used herein, the term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heartbeat. The first heart sound (S1) is the vibrational sound made by the heart during tensing of the mitral valve. The second heart sound (S2) is related to aortic and pulmonic valve closure. The third heart sound (S3) and fourth heart sound (S4) are related to filling of the left ventricle during diastole. A heart sound sensor produces an electrical signal which is representative of mechanical activity of a patient's heart. An example of a heart sound sensor includes an accelerometer or microphone. An approach for measuring heart sounds can be found in Seijko et al., Method and Apparatus for Monitoring of Diastolic Hemodynamics," U.S. Pat. No. 7,115,096, filed on Dec. 30, 2002, which is incorporated herein by reference in its entirety. The evoked response parameter may include at least one of a measured amplitude of a heart sound associated with evoked response, a time of occurrence of a heart sound associated with evoked response, and a power of a heart sound associated with the evoked response.

In some examples, the medical device may classify a heartbeat or cardiac cycle as normal or abnormal based on the classifications for one or more heart sounds detected during the heart beat or cardiac cycle. In such examples, the medical device may confirm that a cardiac rhythm is treatable when one or more heart beats are classified as abnormal, or withhold therapy when one or more heart beats are classified as normal. In other examples, the heart sound signal may include signals representing other acoustic occurrences including, for example, diaphragm movement in response to phrenic nerve stimulation.

Pacing-induced phrenic nerve stimulation, both symptomatic and asymptomatic, may cause unpleasant symptoms and decreased hemodynamic performance for the patient. In various examples consistent with the present disclosure, phrenic nerve stimulation may be both detected, and in response to the detection, avoided in the future.

Pacing-induced phrenic nerve stimulation is particularly of concern when pacing is provided by a left-ventricular lead, such as a left-ventricular quadrapolar lead. This is because a left-ventricular lead may position one or more electrodes in close proximity to the left phrenic nerve. A physician may desire to program the IMD to provide cardiac resynchronization therapy, including left-ventricular pacing, that provides heart function as close to normal while avoiding capturing one or more phrenic nerves with the applied pulses.

In some examples, the disclosure is directed to detecting pacing-induced PNS using a PNS test signal, such as a heart sounds signal, or an accelerometer signal, for example, and in response, reprogramming the IMD to provide CRT in a manner that does not capture the phrenic nerve. In some examples, reprogramming the IMD includes changing one or more pacing vectors to avoid phrenic nerve stimulation. In some examples, reprogramming the IMD includes modifying various pacing parameters such as pulse strength to avoid phrenic nerve stimulation, with or without changing the pacing vectors. In some examples, modification of the pulse strength is first attempted and, if phrenic nerve stimulation is not avoided without compromising cardiac capture, modification of the pacing vector is attempted. The determination of new pulse strength or pacing vector may be made based on information extracted from the PNS test signal. This is possible because sensors such as activity/ posture sensors or heart sound sensors can detect diaphragmatic muscular movement caused by both symptomatic and asymptomatic PNS in the form of a motion artifact or sound artifact, respectively.

As discussed in more detail below with respect to the various figures, both symptomatic and asymptomatic PNS may be detected using a PNS test signal, such as an accelerometer signal, or an acoustic signal. In various examples, IMD is not continuously monitoring the PNS test signal for PNS. Instead, a detection sequence may be initiated at a given time of day, for example. This allows the IMD to save battery power and to perform other functions using the same sensors and processors at other times. In some examples, PNS detection is initiated at times that PNS is most likely to be detected. For example, a PNS detection sequence may be initiated when a patient is lying on his or her left side. In instances where a left-ventricular lead is used to deliver cardiac pacing, phrenic nerve stimulation may occur when the patient is on his or her left side, but not when the patient is in other positions. In another example, a PNS detection sequence may be initiated by a clinician using a monitoring device at a clinic.

For pacing induced PNS, the IMD, or another device that communicates with the IMD, may determine signal artifacts of the sensed PNS test signal just before and after a predetermined timing signal, such as a 150 ms time delay, for example, or just before and after a predetermined cardiac signal, such as a ventricular pace (Vp) beat, and an atrial sense (As) beat, or an atrial pace (Ap) beat. The device determines whether PNS beat criteria have been met based on the determined signal artifacts before and after the predetermined timing signal, or based on the determined signal artifacts before and after the predetermined cardiac signal. If the PNS beat criteria are not satisfied, the beat is determined not to be a PNS beat and the process resumes for the next beat. On the other hand, if the PNS beat criteria are satisfied, the IMD determines that a PNS episode is occurring. For example, as described below, PNS detection of the present disclosure may evaluate presence or absence of PNS on a beat-by-beat basis by detecting an acoustic artifact of a heart sounds signal that occurs after a left ventricular (LV) pace (Vp). While the determination of signal artifacts is described below in reference to signal artifacts occurring before and after a predetermined cardiac signal, it is understood that the determination of signal artifacts may be performed in reference to a timing signal, such as a 150 ms time delay, for example.

The analyzed heart sounds signal data may be digitized by a 16-bit ADC with ±64 mV range sampled at 256 Hz, and bandpass filtered. The absolute value of the filtered heart sounds signal (|FHS|) is determined and a predetermined number of beats are evaluated for PNS at a user selectable voltage and/or polarity. In one example, in order to ensure that the evaluation is completed in less than 3 minutes at an estimated heart rate of 60 bpm for 16 vectors (11×16×1000 ms cycle length=176 s), up to 11 beats are evaluated for PNS at the user selectable voltage output. For each PNS test beat, a PNS window that includes a PreVp window and a PostVp window, and a noise window of the heart sounds signal may be determined for use in evaluating and detecting whether PNS is present. In one example, the PreVp window may include 25 samples before and up to the Vp beat (98 ms), the PostVp window may occur 7 to 21 samples (27 to 82 ms) after the Vp beat for a left-sided device implant, or 20 to 32 ms (78 to 125 ms) after the Vp beat for a right-sided device implant, and the noise window may occur 7 to 80 samples (27 to 313 ms) after the Vp beat.

Signal features of the heart sounds signal, such as one or more of maximum, minimum, range, mean, sum and absolute difference of the signal are calculated within each window. Absolute difference is analogous to standard deviation (SD) and is calculated by subtracting the mean from a signal, summing the absolute value of the resulting time series and dividing by the length of the signal. Heart sound signal features within the noise window are first evaluated for each beat to detect or determine whether the beat is associated with noise, and if noise is not detected for the beat, the heart sound signal features within the PNS window are evaluated for the beat to detect or determine whether the beat is associated with presence of PNS. If the beat is neither a noise beat nor a PNS beat, the beat is classified as a non-PNS beat, and the process continues for the next beat identified by the heart sounds signal until a predetermined number of beats have been evaluated, or a predetermined time period has expired. On the other hand, if the beat is not identified as being a noise beat but is identified as being a PNS beat, the beat is classified as a PNS beat. In either case, i.e., the current beat being a PNS beat or a non-PNS beat, the process continues for the next beat until a predetermined number of beats have been evaluated, a predetermined time period has expired, or a PNS episode is detected based on a predetermined sequence of beats being identified as PNS beats.

In an attempt to avoid PNS when setting pacing parameters, the IMD may step up the pacing pulse amplitude and/or width from the minimal pacing capture threshold to the maximum output of the IMD. In some examples, the IMD may stop the stepping up process when PNS is detected. In some examples where PNS detection is implemented after the pacing parameters have been set, the IMD steps down the amplitude of the pacing pulse after an initial determination of PNS until PNS is no longer detected, so long as cardiac capture is maintained.

In some examples, it may be desirable to determine if a preferred or chosen pacing vector or modality will cause PNS for a specific patient. This may be done by first applying pacing stimulation at the maximum output of the stimulation generator to see if PNS is present or not. If PNS is present, then the IMD may gradually step-down the pacing pulse amplitude until the minimal pacing amplitude that still causes PNS is determined (PNS threshold). If the PNS threshold is above the threshold for capturing the ventricle to provide adequate pacing, then the chosen pacing vector may still be used. If not, then another vector or electrode configuration may be tested until one is found where a pacing pulse may be delivered that provides pacing capture without also stimulating the phrenic nerve.

In some examples, once PNS is detected, the 1 MB, or another device that communicates with the IMD, may modify the pacing parameters to provide pacing that does not compromise the patient's hemodynamics while avoiding PNS. In some examples, the heart sound signal is used to assess the pacing parameters not only for PNS but for overall heart function.

In some examples, the method of detecting PNS, described below, may be performed by another device that communicates with the 1 MB and enables automatic PNS detection using only a heart sound signal. The PNS detection feature may therefore reduce the time required to evaluate PNS at implant and potentially reduce symptomatic PNS post-implant by detecting indications not detected with manual PNS assessment, i.e. visually, by palpation, or under fluoroscopy, for example.

In some examples, phrenic nerve stimulation may be desired. For example, it may be desirable to provide PNS as a substitute for mechanical ventilation in patients with neurological disorders such as central sleep apnea. In such examples, the amount of stimulation applied may be different every few pulses in order to simulate normal breathing patterns. PNS detection using heart sounds may be used to confirm the effectiveness of the attempted phrenic nerve stimulation.

FIG. 1 is a conceptual diagram illustrating an example system 10 that may detect phrenic nerve stimulation. In some examples, system 10 monitors both cardiac electrical activity and heart sounds-based signals. In some examples, system 10 provides stimulation to the cardiac tissue based on a set of parameters, and monitors a signal representative of cardiac electrical activity, e.g., an electrogram (EGM), and a heart sounds signal. Based at least on the heart sounds signal, system 10 determines whether the cardiac stimulation at the present stimulation parameters is causing unwanted phrenic nerve stimulation.

System 10 includes implantable medical device (IMD) 16, which is connected to leads 18, 20 and 22 and is optionally communicatively coupled to programmer 24. IMD 16 senses electrical signals attendant to the depolarization and repolarization of heart 12, e.g., a cardiac EGM, via electrodes on one or more leads 18, 20 and 22 or the housing of IMD 16. In some examples, IMD 16 also delivers cardiac therapy in the form of electrical signals to heart 12 via electrodes located on one or more leads 18, 20 and 22 or a housing of IMD 16. The cardiac therapy may be pacing, cardioversion and/or defibrillation pulses. The IMD 16 may also provide respiratory induction therapy. The respiratory induction therapy includes electrical stimulation to one or more phrenic nerves 36 and 38 via electrodes located on one or more of leads 18, 20 and 22, other leads not illustrated in FIG. 1, or a housing of IMD 16. In some examples, the electrodes used to stimulate phrenic nerves 36 and 38 may be used for both cardiac and phrenic nerve stimulation. IMD 16 also includes one or more heart sound sensors (not shown in FIG. 1) used to detect the occurrence of phrenic nerve stimulation in patient 14. IMD 16 may similarly include or be coupled to other sensors, such as one or more accelerometers, for detecting other physiological parameters of patient 14, such as activity or posture.

In some examples, programmer 24 takes the form of a handheld computing device, computer workstation or networked computing device that includes a user interface for presenting information to and receiving input from a user. A user, such as a physician, technician, surgeon, electrophysiologist, or other clinician, may interact with programmer 24 to retrieve physiological or diagnostic information from IMD 16. A user may also interact with programmer 24 to program IMD 16, e.g., select values for operational parameters of the IMD or initiate a phrenic nerve stimulation detection sequence.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In other examples, programmer 24 may be located remotely from IMD 16, and communicate with IMD 16 via a network.

Leads 18, 20, 22 extend into the heart 12 of patient 14 to sense electrical activity of heart 12 and/or deliver electrical stimulation to heart 12. The leads may also deliver electrical stimulation to phrenic nerve 38. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In some examples, RA lead 22 may be used to stimulate right phrenic nerve 36. In some examples, LV coronary sinus lead 20 may be used to stimulate left phrenic nerve 38.

Techniques for detecting stimulation of one or more of phrenic nerves 36 and 38 are primarily described herein as being performed by IMD 16, e.g., by processing circuitry of a processor of IMD 16. In other examples, some or all of the functions ascribed to IMD 16 or a processor thereof may be performed by one or more other devices such as programmer 24, or a processor thereof. For example, IMD 16 may process cardiac and/or heart sound signals to determine whether therapy should continue to be delivered based on current parameters, or whether adjustments to the parameters should be made, and control the parameters used by IMD 16 to deliver the therapy. Alternatively, programmer 24 may process cardiac and/or heart sound signals received from IMD 16 to determine whether therapy should continue to be delivered based on current parameters or whether adjustments to the parameters should be made, and control according to what parameters IMD 16 delivers the therapy. Furthermore, although described herein with respect to an IMD, in other examples, the techniques described herein may be performed or implemented in an external medical device, which may be coupled to a patient via percutaneous or transcutaneous leads. In some examples, various functions of IMD 16 may be carried out by multiple IMDs in communication with one another.

Figure 2:
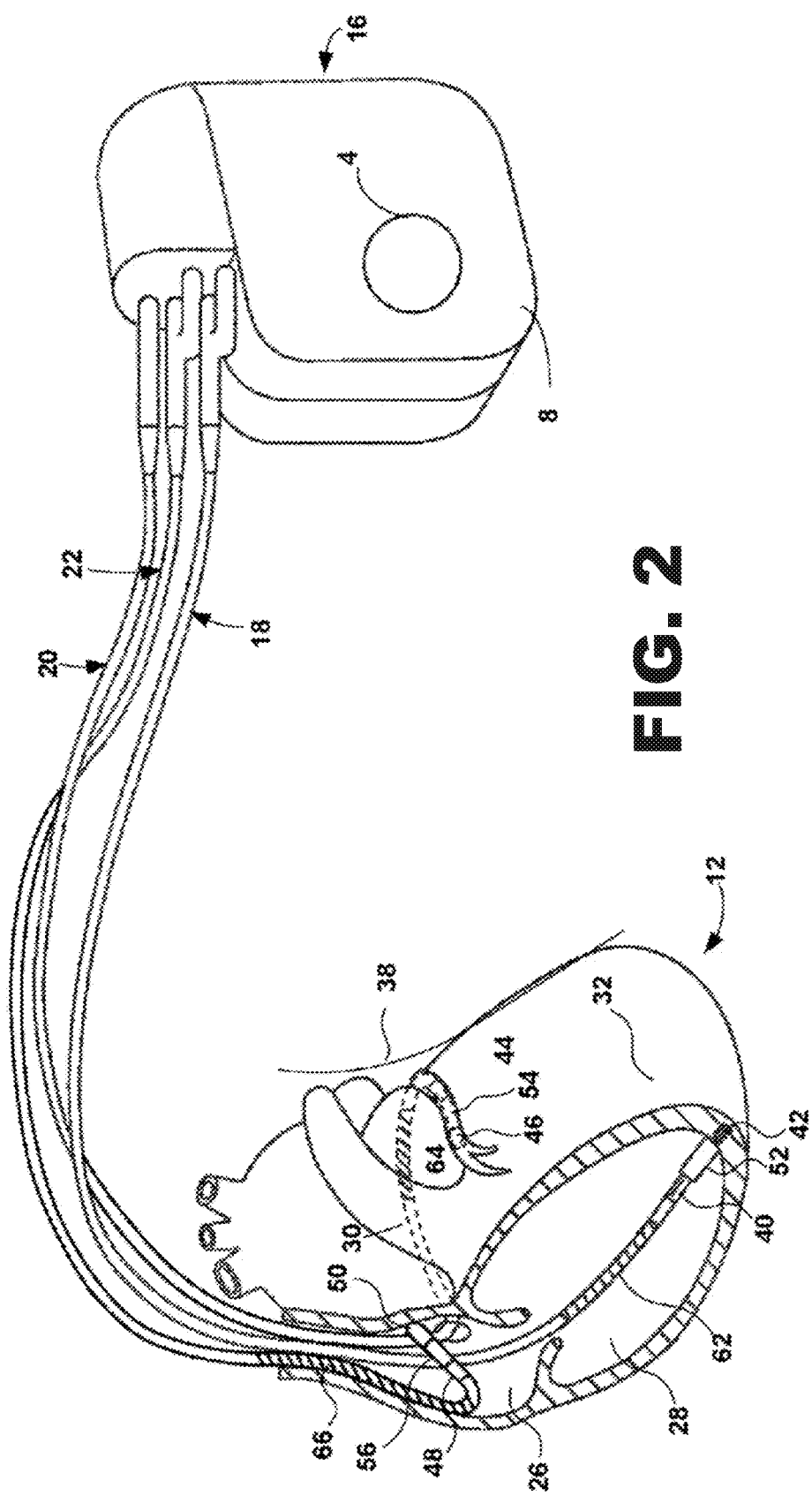
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative examples, not shown in FIG. 2, one or more of leads 12, 20 and 22, such as left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes, 40, 42, 44, 46, 48, 50, 62, 64 and 66 is electrically coupled to a respective conductor within the lead body of its associated lead 18, 20, 22, and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioversion and defibrillation pulses, as well as a sensing module for sensing electrical signals attendant to the depolarization and repolarization of heart 12. IMD 16 may also include a heart sounds sensor that monitors acoustic noises including heart sounds and sounds resulting from phrenic nerve stimulation, for example. The heart sounds sensor may be, for example, an accelerometer or a microphone. The heart sounds sensor may be enclosed within housing 8. Alternatively, the heart sounds sensor may be integrally formed with or carried on an outer surface of housing 8, carried on or within a lead coupled to IMD 16, such as one or more leads 18, 20 and 22, or be a separate, remote sensor that wirelessly communicates with IMD 16, programmer 24 or any other device described herein.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

In some examples, IMD 16 delivers stimulating pulses via bipolar combinations of electrodes chosen based on EGM signals and/or heart sound signals as analyzed by a signal analyzer within IMD. For example, bipolar combinations of electrodes 40, 42, 44, 46, 48, and 50 are used to produce depolarization of cardiac tissue of heart 12. In addition, phrenic nerve stimulation pulses may be delivered by various electrodes used to provide cardiac stimulation, and which electrodes may be chosen to deliver phrenic nerve stimulation based on the location of the electrodes. In some examples, IMD 16 delivers stimulation to either cardiac tissue or the phrenic nerve via any of electrodes 40, 42, 44, 46, 48 and 50 in combination with housing electrode 4 in a unipolar configuration. In some examples, the choice of electrodes delivering cardiac and phrenic nerve electrical stimulation may be based on default settings. Furthermore, IMD may deliver cardioversion or defibrillation pulses to heart 12 or pulses to phrenic nerves 36 and 38 via any combination of elongated electrodes 62, 64, 66 and housing electrode 4.

The illustrated numbers and configurations of leads 18, 20 and 22 and electrodes are merely examples. Other configurations, i.e., numbers and positions of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more epicardial or subcutaneous leads not positioned within the heart. For example, a lead may be positioned to provide one or more electrodes in proximity to or in contact with phrenic nerve 36 or phrenic nerve 38. As another example, system 10 may include an additional lead that carries a heart sound sensor positioned such that signals generated by the heart sounds sensor include information regarding a patient's respiratory activity including, for example, inspiration and expiration.

Figure 3:
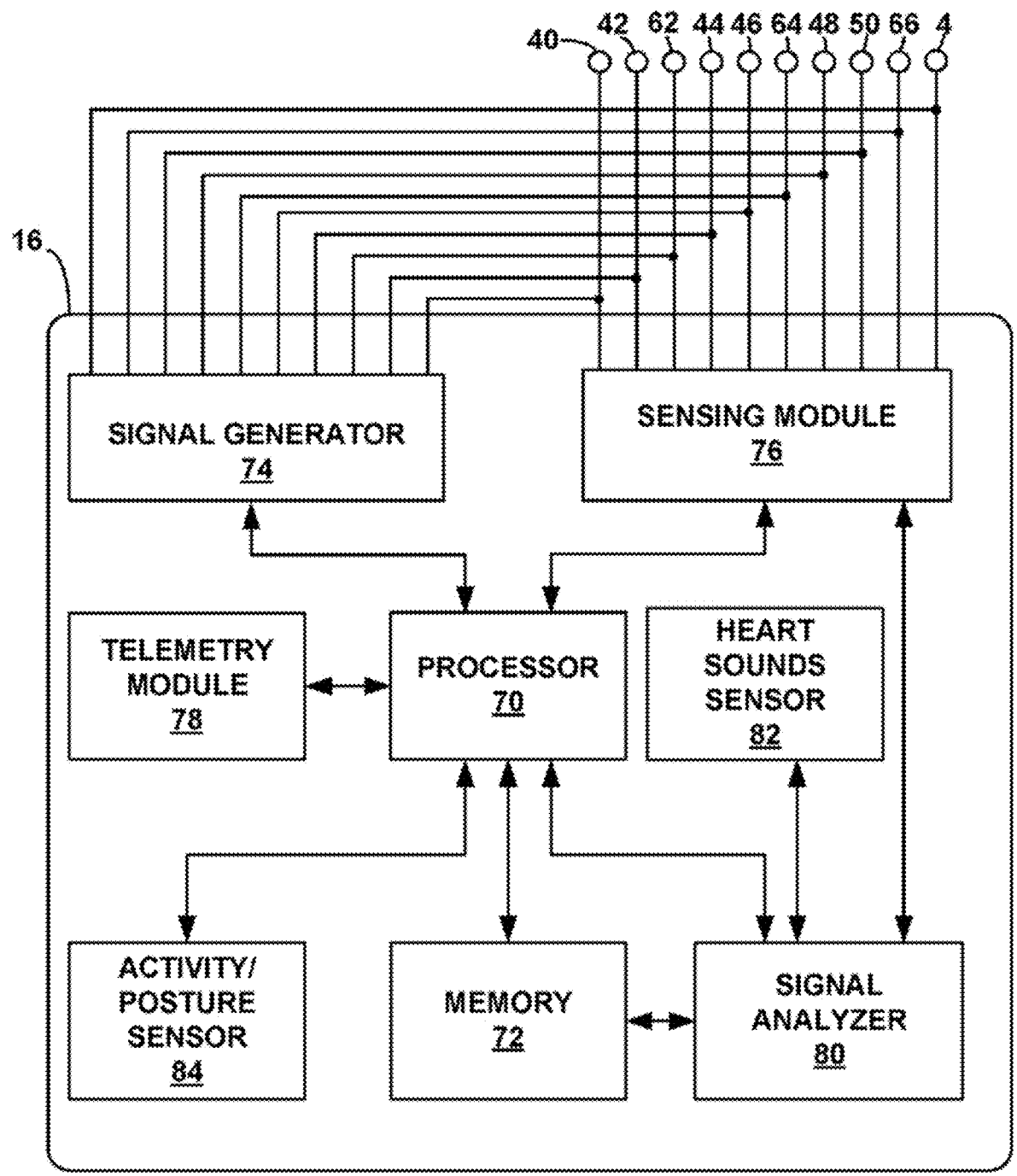
FIG. 3 is a block diagram illustrating an example configuration of the IMD of FIG. 1.

FIG. 3 is a block diagram illustrating an example configuration of IMD 16. In the illustrated example, IMD 16 includes a processor 70, memory 72, signal generator 74, sensing module 76, telemetry module 78, a signal analyzer 80, a heart sounds sensor 82, and an activity/posture sensor 84. Memory 72 includes computer-readable instructions that, when executed by processing circuitry of processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs. The therapy programs may be selected by the processor 70 based on information from the signal analyzer 80.

Signal generator 74 is configured to generate and deliver electrical stimulation therapy to patient 12. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver stimulating pulses to phrenic nerves 36 and 38 via at least two of electrodes 4, 40, 42, 44, 46, 48, 50, 62, 64 and 66. In addition, in some examples, signal generator 74 may deliver pacing pulses, defibrillation shocks or cardioversion shocks to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events. Signal analyzer 80 may use the detection in connection with sensed heart sounds to determine one or more cardiac metrics.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythm. In some examples, the signal analyzer 80 employs digital signal analysis techniques to characterize the digitized signals from the wide band channel. The digitized signals may be used in conjunction with heart sound signals to determine if phrenic nerve stimulation has occurred.

Processor 70 may initiate a phrenic nerve stimulation detection sequence in response to detecting an activation event. In some examples, processor 70 may receive an activation signal from programmer 24 via telemetry module 78, which may be the activation event, before initiating phrenic nerve stimulation detection. In some examples, the activation event may be one or more of an activity/posture detected via activity posture sensor 84, signal analyzer 80, memory 72, and sensing module 76. In some examples, processor 70 may initiate phrenic nerve stimulation detection at a given time. For example, memory 72 may provide a program to processor 70 wherein phrenic nerve stimulation detection occurs every day at a predetermined time. In such cases the activation event is the time of day. In other examples, processor 70 may initiate phrenic nerve stimulation detection during a predetermined time range when predefined parameters are met. For example, processor 70 may initiate phrenic nerve stimulation detection between 10 p.m. and 5 a.m. when an activation event, such as activity/ posture sensor 84 indicating that patient 12 is lying down, occurs. In some specific examples, processor 70 may initiate phrenic nerve stimulation detection in response to an activation event such as an indication from the activity/posture sensor 84 that patient 12 is lying on his or her left side is received. In some examples, processor 70 may initiate a phrenic nerve stimulation detection sequence based on an activation event such as one or more pacing parameters changing. In some examples, processor 70 may initiate a phrenic nerve stimulation detection sequence in conjunction with a pacing parameter optimization process.

In the example in FIG. 3 (e.g., to detect the presence of phrenic nerve stimulation), IMD 16 also includes heart sound sensor 82 and signal analyzer 80. Heart sound sensor 82 generates an electrical signal based on sensed acoustics or vibrations originating from heart movement and diaphragm movement, for example. In some examples, heart sound sensor 82 may comprise more than one sensor. For example, the heart sound sensor may include multiple individual sensors. In some examples, heart sound sensor 82 is an acoustic sensor, such as an accelerometer, microphone, or piezoelectric device. The acoustic sensor picks up sounds resulting from the activation of the diaphragm in addition to the heart sounds S1-S4.

In the illustrated example of FIG. 3, heart sounds sensor 82 is enclosed within housing 8 of IMD 16. In some examples, heart sounds sensor 82 may be formed integrally with or on an outer surface of housing 8. In some examples, heart sounds sensor 82 is located on one or more leads that are coupled to IMD 16 or may be implemented in a remote sensor that wirelessly communicates with IMD 16. In such cases, heart sounds sensor 82 may be electrically or wirelessly coupled to circuitry contained within housing 8 of IMD 16. In some examples, a remote heart sound sensor 82 may be wirelessly connected to programmer 24.

Signal analyzer 80 receives the electrical signal generated by heart sounds sensor 82. In one example, signal analyzer 80 may process the sensor signal generated by heart sounds sensor 82 to detect occurrences of phrenic nerve stimulation. In some examples, signal analyzer 80 processes the heart sound sensor signal to generate an envelope signal, detect occurrences of phrenic nerve stimulation, detect other hearts sounds, extract heart sound features from the detected heart sound signal, and assess various cardiac metrics. The cardiac metrics may provide a method to assess the electrical-mechanical functioning of the heart 12. In some examples, the detected heart sound features, both those associated with phrenic nerve stimulation, and those associated with other heart activity, may be compared to values for each feature stored in memory 72. The heart sound features may then be classified based on the deviation from the stored values. The heart sound features and/or their classifications may be used to determine whether phrenic nerve stimulation has occurred, and to assess the function of heart 12.

A heart sound based indication may be output from signal analyzer 80 to processor 70. In some examples, the heart sound features are output to the processor 70. The processor 70 may determine whether phrenic nerve stimulation has occurred based on the information received from signal analyzer 80. In some examples, processor may adjust stimulation provided by signal generator 74 based on the heart sounds-based information received.

In various examples one or more of the functions attributed to signal analyzer 80 may be performed by processor 70. In some examples, signal analyzer 80 may be implemented as hardware, software, or some combination thereof. For example, the functions of signal analyzer 80 described herein may be implemented in a software process executed by processor 70.

Figure 4:
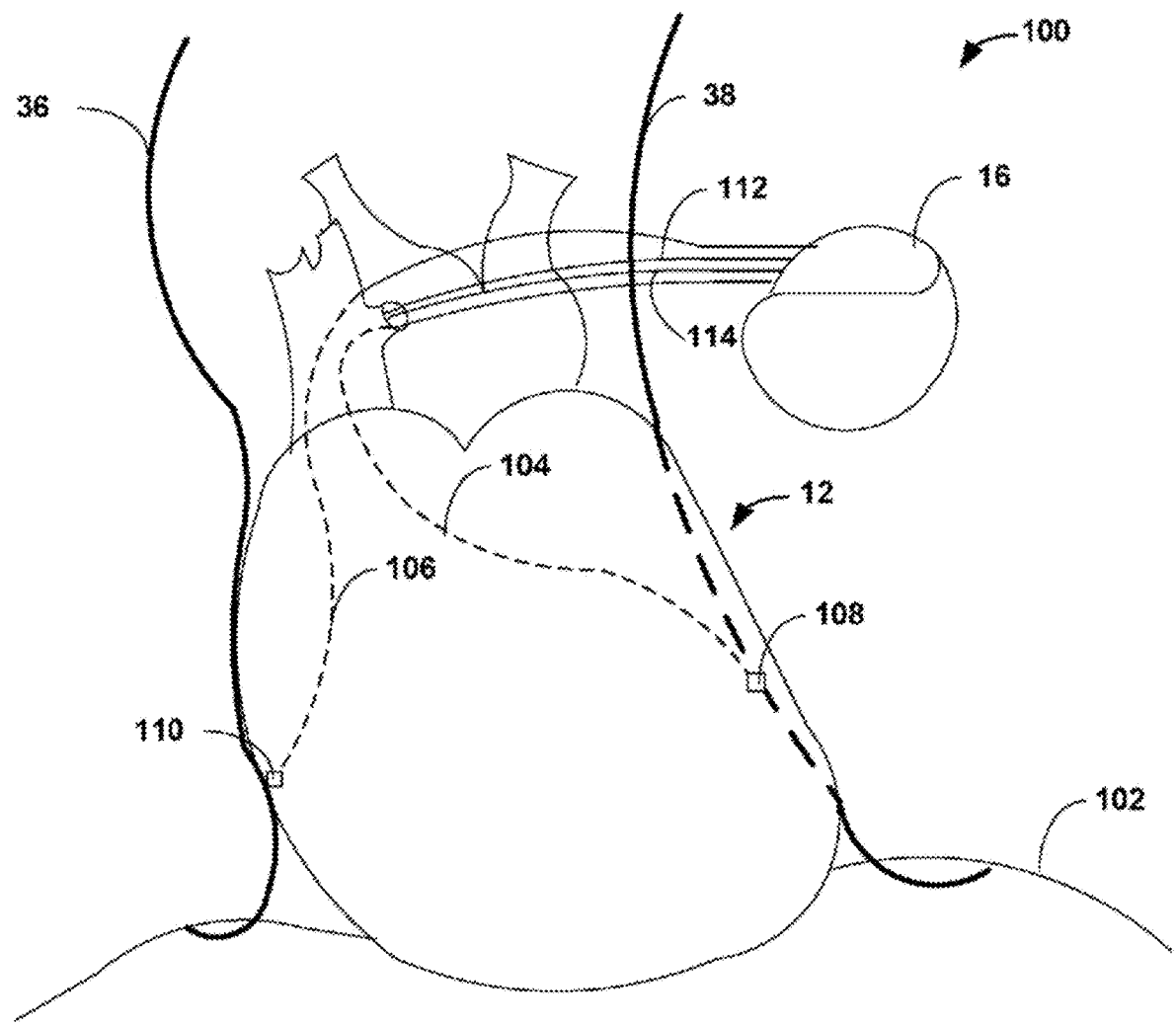
FIG. 4 is a conceptual diagram illustrating an example system that delivers phrenic nerve stimulation, consistent with an example of the present disclosure.

FIG. 4 is a conceptual diagram illustrating an example system 100 for detecting phrenic nerve stimulation using heart sounds. The system 100 includes IMD 16 that monitors heart sounds based signals and determines if the phrenic nerve is being stimulated based on the heart sounds-based signal. In some examples IMD 16 may also monitor cardiac electrical activity signals, e.g., EGM signals, and may provide cardiac tissue stimulation. In some examples, the detection of phrenic nerve stimulation may trigger an optimization protocol for the pacing parameters used to provide the cardiac tissue stimulation. In some examples, the system 100 detects the occurrence of phrenic nerve stimulation and provides an indication of the phrenic nerve stimulation to a remote device, for example, programmer 24.

System 100 includes IMD 16, which is connected to leads 104, 106, 112 and 114, and is optionally communicatively coupled to a programmer (not shown in FIG. 4). IMD 16 senses various signals attendant to activation of diaphragm 102 in response to electrical stimulation of phrenic nerves 36 and 38. In some examples, leads 104 and 106 are positioned proximate to the phrenic nerves. The stimulation may be provided to phrenic nerves 36 and 38 via electrodes 108 and 110. Leads 104 and 106 may be intracardiac leads including additional electrodes (not shown) providing cardiac stimulation, and leads 112 and 114 may be intracardiac leads, e.g., for providing cardiac stimulation. In some examples, electrodes 108 and 110 may be cuff electrodes that at least partially surround phrenic nerves 36 and 38, respectfully.

In some examples, IMD 16 senses electrical signals attendant to the depolarization and repolarization of heart 12, e.g., a cardiac EGM, via electrodes on one or more of leads 104, 106, 112 and 114, or the housing of IMD 16. In some examples, IMD 16 delivers cardiac therapy in the form of electrical signals to heart 12 via electrodes located on one or more of leads 104, 106, 112 and 114. IMD may also include, or be coupled to, other sensor such as one or more accelerometers for detecting other physiological parameters of a patient, such as activity or posture.

Techniques for monitoring stimulation of one or more of phrenic nerves 36 and 38 are primarily described herein as being performed by IMD 16, e.g., by a processor of IMD 16. For example, IMD 16 may process heart sounds signals to determine whether the IMD 16 should continue to deliver based on current parameters, or whether adjustments to the parameters should be made. The processor in IMD 16 may also control the parameters used by 16 to deliver therapy. It is understood that, in another example, the techniques of the present disclosure may also be performed by another device that communicates with the IMD 16, such as a programming and/or monitoring device at a clinic.

Figure 5:
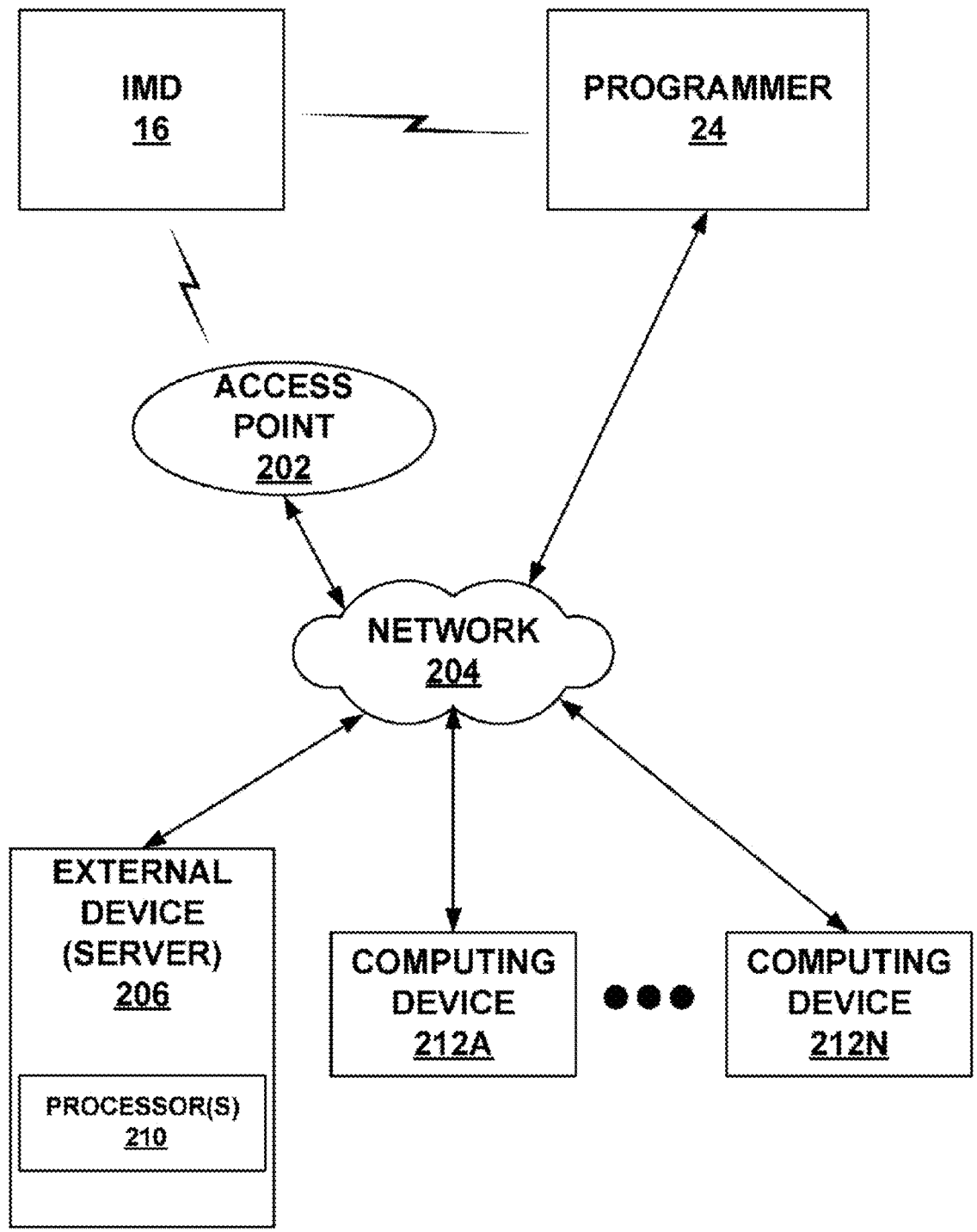
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 206, and one or more computing devices 212A-212N that are coupled to the IMD 16 and programmer 24 shown in FIG. 1 via a network 204. Network 204 may be generally used to transmit diagnostic information (e.g., the occurrence of phrenic nerve stimulation) from an IMD 16 to a remote external computing device. In some examples, the heart sounds and/or EGM signals may be transmitted to an external device for processing.

In some examples, the IMD 16 transmits information during predetermined windows of time. In some examples, the windows of transmission align with a window during which an activation event may result in the initiation of a phrenic nerve detection sequence. In some examples, network 204 may also transmit information from IMD 16 regarding the activation event that triggered the phrenic nerve stimulation to the remote external computing device.

In some examples, the information transmitted by IMD 16 may allow a clinician or other healthcare professional to monitor patient 14 remotely. In some examples, IMD 16 may use its telemetry module 78 to communicate with programmer 24 via a first wireless connection, and to communicate with an access point 202 via a second wireless connection, e.g., at different times. In the example of FIG. 5, access point 202, programmer 24, server 206, and computing devices 212A-212N are interconnected, and able to communicate with each other, through network 204. In some cases, one or more of access point 202, programmer 24, server 206, and computing devices 212A-212 N may be coupled to network 204 via one or more wireless connections. IMD 16, programmer 24, server 206, and computing devices 212A-212N may each comprise one or more processors, such as one or more microprocessors, DSPs, ASICs, FPGAs, programmable logic circuitry, or the like, that may perform various functions and operations, such as those described herein.

Access point 202 may comprise a device that connects to network 204 via any of a variety of connections, such as telephone dial-up, digital subscriber line (DSL), or cable modem connections. In other examples, access point 202 may be coupled to network 204 through different forms of connections, including wired or wireless connections. In some examples, access point 202 may be co-located with patient 14 and may comprise one or more programming units and/or computing devices (e.g., one or more monitoring units) that may perform various functions and operations described herein. For example, access point 202 may include a home-monitoring unit that is co-located with patient 14 and that may monitor the activity of IMD 16. In some examples, server 206 or computing devices 212 may control or perform any of the various functions or operations described herein, e.g., determine, based on heart sounds, whether the phrenic nerve is being stimulated.

In some cases, server 206 may be configured to provide a secure storage site for archival of diagnostic information (e.g., occurrence of phrenic nerve stimulation and attendant circumstances such as pacing parameters) that has been collected and generated from IMD 16 and/or programmer 24. Network 204 may comprise a local area network, wide area network, or global network, such as the Internet. In some cases, programmer 24 or server 206 may assemble PNS information in web pages or other documents for viewing by and trained professionals, such as clinicians, via viewing terminals associated with computing devices 212. The system of FIG. 5 may be implemented, in some aspects, with general network technology and functionality similar to that provided by the Medtronic CareLink® Network developed by Medtronic, Inc., of Minneapolis, Minn.

In the example of FIG. 5, external server 206 may receive heart sound information from IMD 16 via network 204. Based on the heart sound information received, processor(s) 210 may perform one or more of the functions described herein with respect to signal analyzer 80 and processor 70. In some examples, an external device such as server 206 or computing devices 212 may provide an activation signal to IMD 16 via network 204. In response to the activation signal, IMD 16 may initiate a phrenic nerve detection sequence consistent with one or more of the methods described below, for example. In some examples, heart sound signals are transmitted to the external device that sent the activation signal. The external device, such as server 206 processes the signals using the phrenic nerve detection features described below to determine whether phrenic nerve stimulation has occurred.

Figure 6:
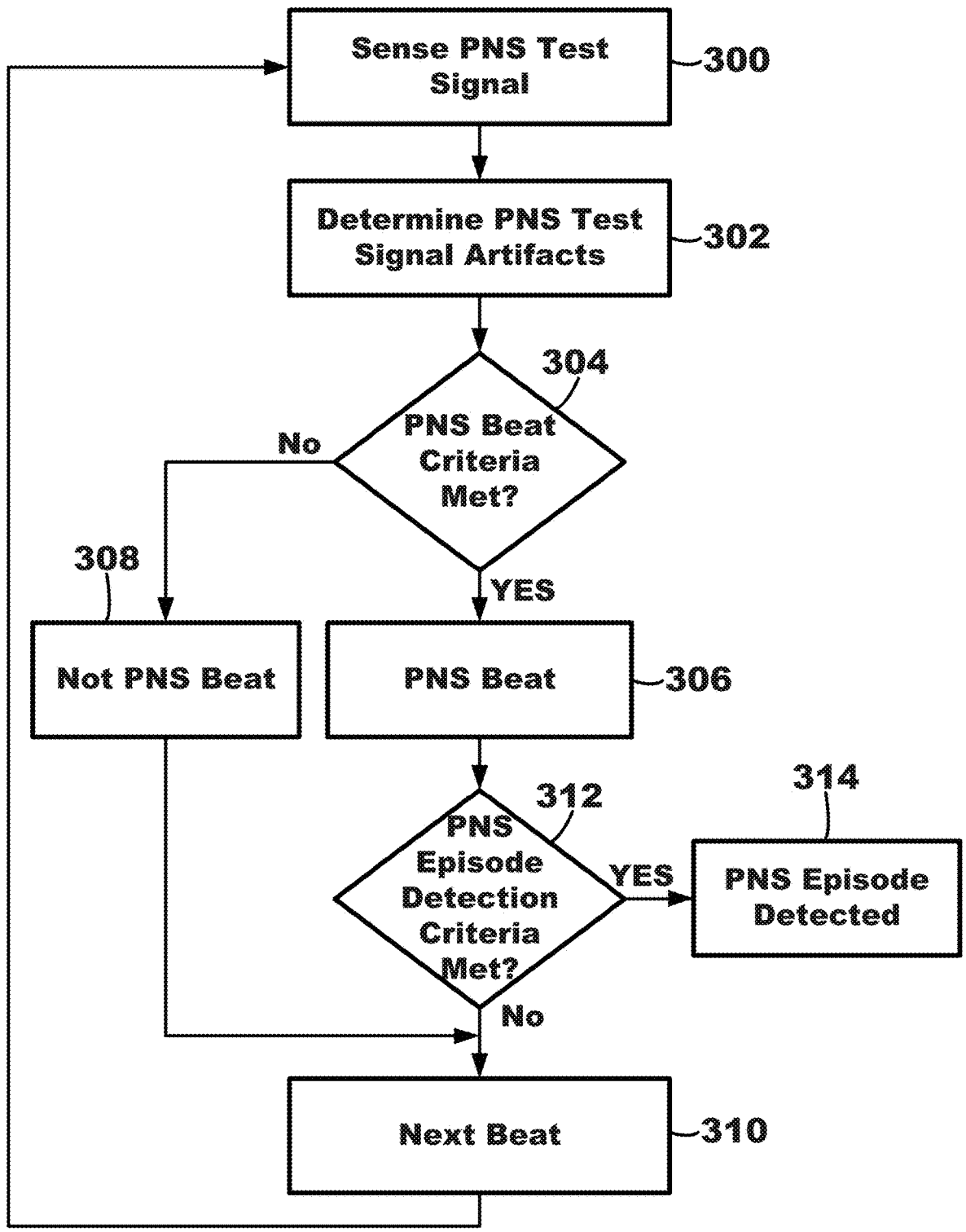
FIG. 6 is a flowchart of a method of determining the presence of phrenic nerve stimulation in a medical device, according to an example of the present disclosure.

FIG. 6 is a flowchart of a method of determining the presence of phrenic nerve stimulation in a medical device, according to an example of the present disclosure. As illustrated in FIG. 6, in order to determine the presence of phrenic nerve stimulation, the device, such as IMD 16, for example, or a device or monitoring system external to IMD 16, may perform the determination on a beat-by-beat basis by sensing a PNS test signal that is sensitive to contraction of a diaphragm of a patient, such as an acoustic signal or an accelerometer signal, for example, Block 300. The device determines signal artifacts of the sensed PNS test signal which occur during a post cardiac signal window after a predetermined cardiac signal and a pre-cardiac signal window before the predetermined cardiac signal, Block 302. Based on the determined signal artifacts of the PNS test signal, the device determines whether PNS beat criteria have been met for the beat, Block 304, and if the PNS beat criteria have been met for the beat, Yes in Block 304, the beat is identified as a PNS beat, Block 306. On the other hand, if the PNS beat criteria have not been met for the beat, No in Block 304, the beat is identified as not being a PNS beat, Block 308, and the process is repeated for the next beat, Block 310.

When the current beat is identified as being a PNS beat, Block 306, the device determines whether PNS episode criteria have been met, Block 312. If the PNS episode criteria have not been met, No in Block 312, the process is repeated for the next beat, Block 310. If the PNS episode criteria have been met, Yes in Block 312, the device determines that a PNS episode is occurring, Block 314. In one example, PNS episode detection criteria are determined to be met, Yes in Block 312, once a specific number or sequence of PNS beats have been detected. For example, PNS detection episode criteria may be met if a predetermined number of consecutive beats, such as three beats for example, are identified on a beat-by-beat basis as PNS beats. According to another example, the PNS episode detection criteria may be met if PNS is detected for every predetermined sequential beat for a total number of beats, such as for every third beat for three total beats, i.e., beat(i), beat (i−3), beat (i−6), for example. Once the PNS episode detection criteria are met and therefore a PNS episode is detected, Block 314, the device may generate an alert, adjust the pacing vector for delivery of the pacing therapy, or suspend delivery of the pacing therapy. In one example, the device may suspend determining the presence of PNS in response to the determination as to whether the PNS episode detection criteria having been being determined for 11 consecutive beats without a PNS episode being detected.

Therefore, in the example of FIG. 6, PNS test signal features within the PNS window are evaluated for the beat to detect or determine whether the beat is associated with presence of PNS. If the beat is not determined to be a PNS beat, the beat is classified as a non-PNS beat, and the process continues for the next beat identified by the PNS test signal until a predetermined number of beats have been evaluated, or a predetermined time period has expired. On the other hand, if the beat is determined to be a PNS beat, the beat is classified as a PNS beat. In either case, i.e., the current beat being a PNS beat or not being a PNS beat, the process continues for the next beat until either a predetermined number of beats have been evaluated, a predetermined time period has expired, or a PNS episode is detected based on a predetermined number or sequence of beats being identified, on a beat-by-beat basis, as PNS beats.

Figure 7:
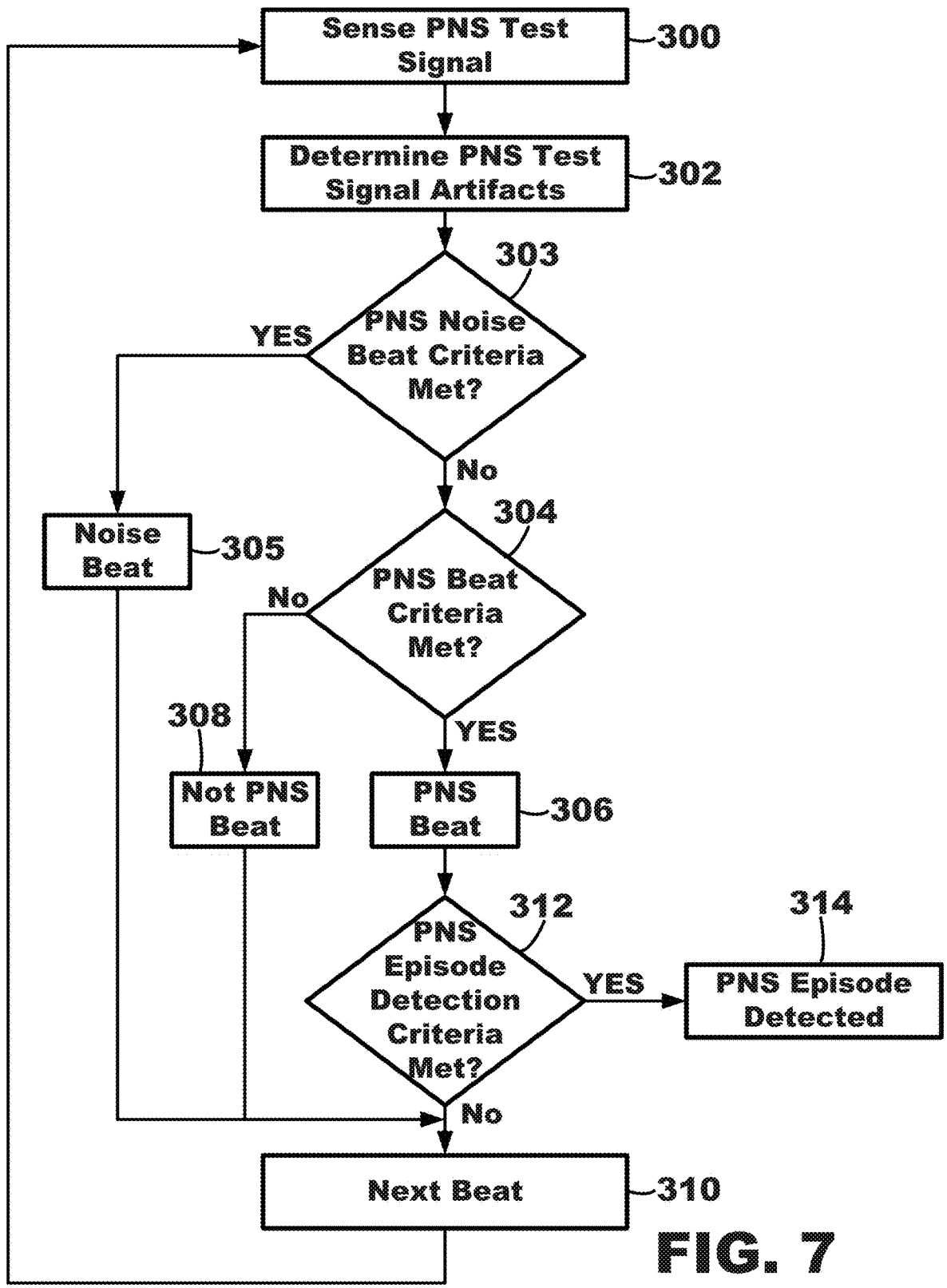
FIG. 7 is a flowchart of a method of determining the presence of phrenic nerve stimulation in a medical device, according to an example of the present disclosure.

FIG. 7 is a flowchart of a method of determining the presence of phrenic nerve stimulation in a medical device, according to an example of the present disclosure. In certain instances, it may be desirable to ensure that the determination of a beat being a PNS beat does not occur as a result of noise occurring in the PNS test signal. For example, as illustrated in FIG. 7, in order to determine the presence of phrenic nerve stimulation, the device may sense a PNS test signal that is sensitive to contraction of a diaphragm of a patient, such as an acoustic signal or an accelerometer signal, Block 300. The device determines, on a beat-by-beat basis, signal artifacts of the test signal for each beat, Block 302, which occur during a noise window extending over a period of time subsequent to the sensed predetermined cardiac signal, in addition to a pre-cardiac signal window extending over a period of time prior to the sensed predetermined cardiac signal and a post-cardiac signal window extending a period of time subsequent to the sensed predetermined cardiac signal. Based on the determined signal artifacts of the noise window, the device determines whether PNS noise criteria have been met, Block 303. If the PNS noise criteria have been met, Yes in Block 303, the beat is determined to be a noise beat, Block 305, and the process is repeated for the next beat, Block 310. If the PNS noise criteria have not been met, No in Block 303, the device determines whether PNS beat criteria have been met for the beat, Block 304. If the PNS beat criteria have been met for the beat, Yes in Block 304, the beat is identified as a PNS beat, Block 306. On the other hand, if the PNS beat criteria have not been met for the beat, No in Block 304, the beat is identified as not being a PNS beat, Block 308, and the process is repeated for the next beat, Block 310.

Each time the current beat is both not identified as being a noise beat and identified as being a PNS beat, Block 306, the device determines whether PNS episode criteria have been met, Block 312. If the PNS episode criteria have not been met, No in Block 312, the process is repeated for the next beat, Block 310. If the PNS episode criteria have been met, Yes in Block 312, the device determines that a PNS episode is occurring, Block 314.

In this way, using only the PNS test signal, each beat is first evaluated to determine whether the beat is a noise beat, and if the beat is not a noise beat, the presence of PNS is evaluated for the beat based on the PNS test signals to determine whether the beat is a PNS beat. If the beat is both determined not to be associated with noise, and to be a PNS beat, the device determines whether PNS episode detection criteria have been met. The determination whether PNS episode detection criteria have been met may be based on a specific number or sequence of PNS beats being detected. For example, PNS episode detection criteria may be met if a predetermined number of consecutive beats, such as three beats for example, are identified on a beat-by-beat basis as PNS beats. According to another example, PNS episode detection criteria may be met if PNS is detected for every predetermined sequential beat for a total number of beats, such as for every third beat for three total beats, i.e., beat(i), beat (i−3), beat (i−6), for example. Once the PNS episode detection criteria are met, and therefore a PNS episode is detected, Block 312, the device may generate an alert, adjust the pacing vector for delivery of the pacing therapy, or suspend delivery of the pacing therapy. In one example, the device may suspend determining of a PNS episode in response to a determination as to whether the PNS noise criteria and the PNS beat criteria having been performed for 11 consecutive beats.

Therefore, in the example of FIG. 7, PNS test signal features within the noise window are first evaluated for the beat to detect or determine whether the beat is associated with noise. If noise is not detected for the beat, the PNS test signal features within the PNS window are evaluated for the beat to detect or determine whether the beat is associated with presence of PNS. If the beat is neither a noise beat nor a PNS beat, the beat is classified as a non-PNS beat, and the process continues for the next beat identified by the PNS test signal until a predetermined number of beats have been evaluated, or a predetermined time period has expired. On the other hand, if the beat is not determined to be a noise beat and is determined to be a PNS beat, the beat is classified as a PNS beat. In either case, i.e., the current beat being a PNS beat or not being a PNS beat, the process continues for the next beat until either a predetermined number of beats have been evaluated, a predetermined time period has expired, or a PNS episode is detected based on a predetermined number or sequence of beats being identified, on a beat-by-beat basis, as PNS beats.

Figure 8:
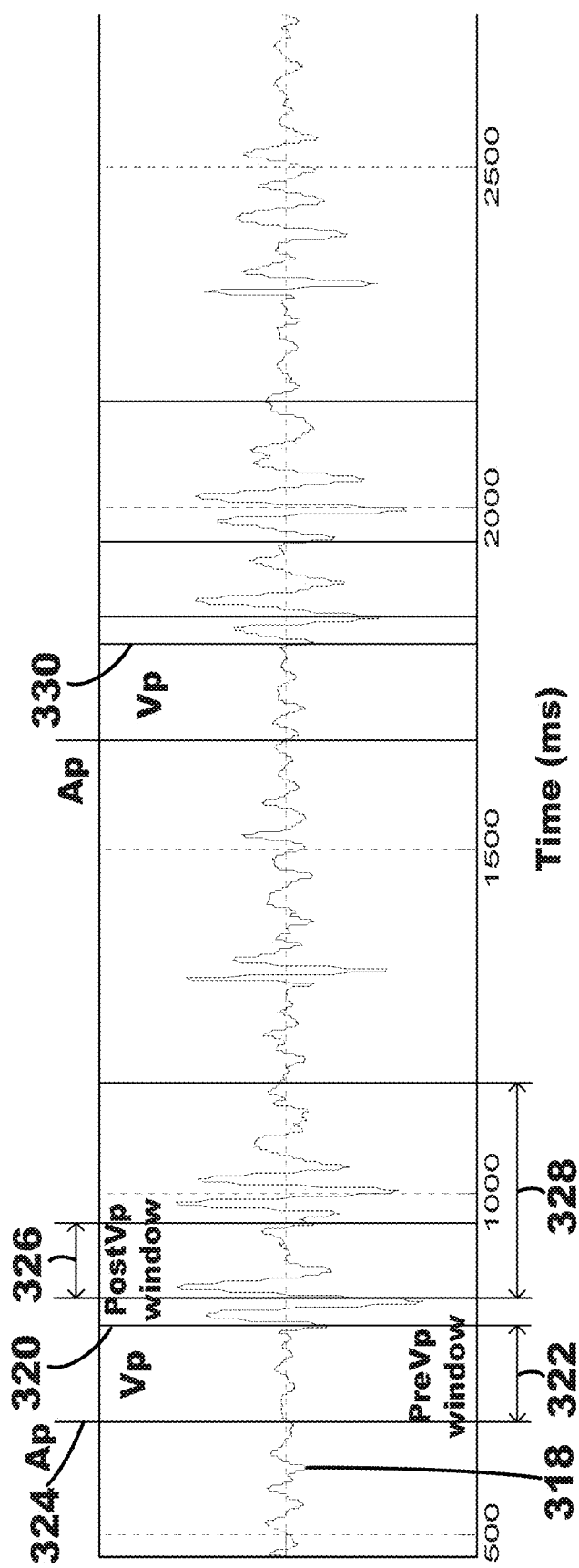
FIG. 8 is a graphical representation of determining of acoustic artifacts of a heart sound signal for determining the presence of phrenic nerve stimulation in a medical device, according to an example of the present disclosure.

FIG. 8 is a graphical representation of determining of acoustic artifacts of a heart sound signal for determining the presence of phrenic nerve stimulation in a medical device, according to an example of the present disclosure. According to one example, the PNS test signal may a heart sounds signal sensed by heart sounds sensor 82, and the predetermined cardiac signal may be a Vp beat sensed by sensing module 76. In other embodiments, the predetermined cardiac signal utilized may be a right atrial pace (Ap) beat, or a right atrial sense (As) beat, for example. In an example in which the PNS test signal is a heart sounds signal and the predetermined cardiac signal utilized is a Vp beat, the device, such as IMD 16, for example, or a device or monitoring system external to IMD 16, determines the presence of a PNS episode using acoustic artifacts of the heart sound signal that occur during a Vp beat on a beat-by-beat basis. The sensed heart sound signal data may be digitized by a 16-bit ADC with ±64 mV range sampled at 256 Hz, and bandpass filtered. The absolute value of the filtered heart sound signal (|FHS|) is determined, and a predetermined number of beats are evaluated for PNS at a user selectable voltage and/or polarity.

In particular, as illustrated in FIG. 8, the device may determine acoustic artifacts from a sensed heart sounds signal 318 associated with a VP beat 320 and identifies a PNS window that includes a pre-ventricular pace (PreVp) window 322 and a post ventricular pace (PostVp) window 326 for the Vp beat 320. According to another example, that includes detecting whether the current beat is a noise beat, in order to determine acoustic artifacts from a sensed heart sounds signal 318 associated with a VP beat, the device identifies a noise window 328 for the beat 320, in addition to a PNS window that includes the pre-ventricular pace (PreVp) window 322 and the post ventricular pace (PostVp) window 326.

According to one example, the PreVp window 322 may extend to the beat 320 from a point 324 along the heart sounds signal 318 that is a predetermined time period prior to the beat 320, such as an atrial pace (Ap) beat. Both the PostVp window 326 and the noise window 328 extend during a predetermined time period of the heart sounds signal 318 after the beat 320, with the noise window extending beyond the PostVp window 328. In one example, the PreVp window 322 may extend 25 samples (98 ms) prior to and including the beat 320, the Post Vp window 326 may extend for the time period extending between 27 ms and 83 ms after the beat 320, i.e., for the sample period between the $7^{th}$ sample and the 21st sample after the beat 320, and the noise window 328 may extend for the time period extending between 27 ms and 313 ms after the beat 320, i.e., for the sample period between the $7^{th}$ sample and the 80 sample after the beat 320. In another example, the Pre Vp window 322 may be less than 25 samples before and including the beat 320 if either the paced AV-delay (PAV) or the sensed AV-delay (SAV) is less than 25 samples. In another example, the Pre Vp window 322 may be 150 ms.

Figure 9:
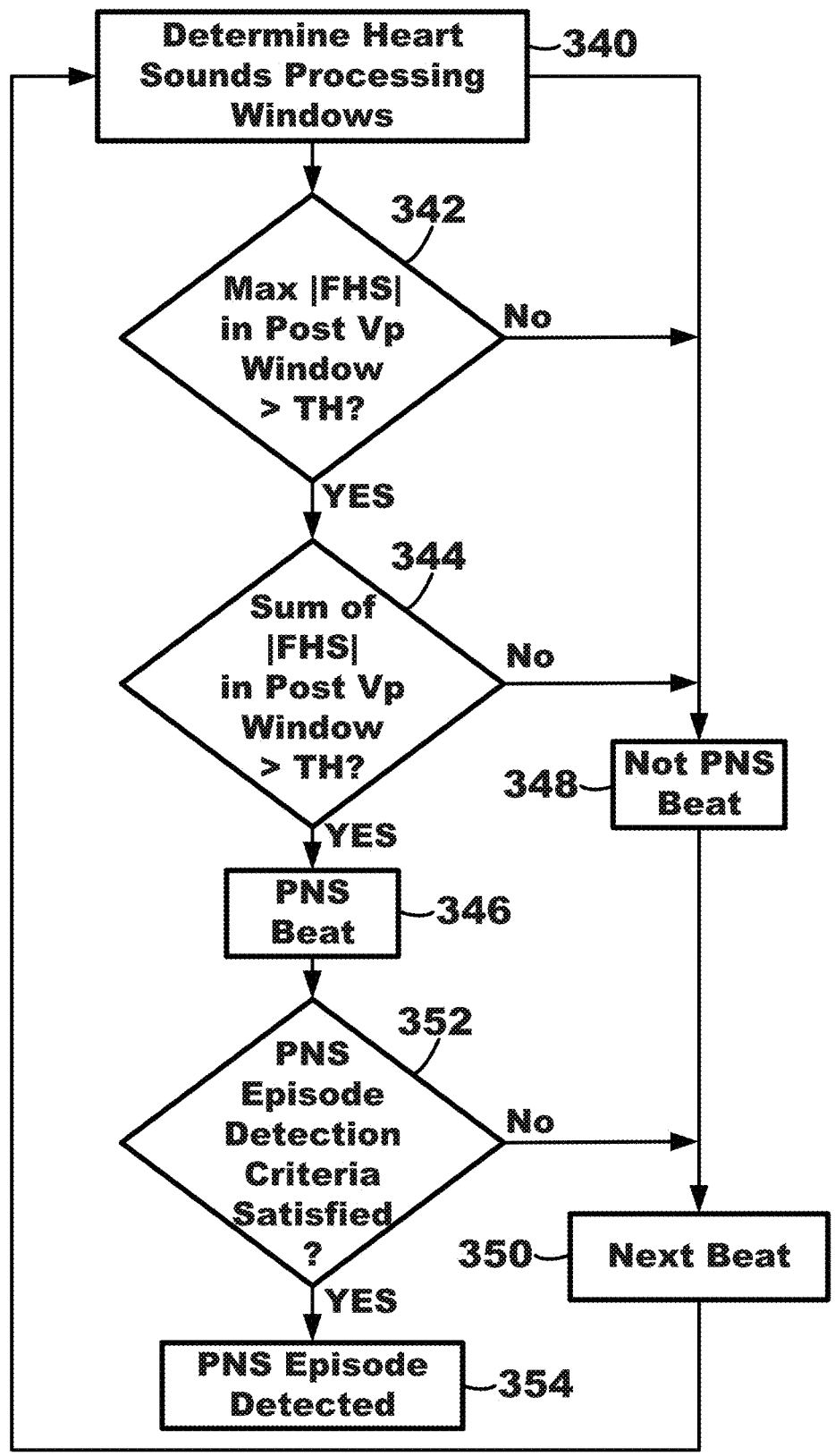
FIG. 9 is a flowchart of a method of determining the presence of phrenic nerve stimulation in a medical device, according to an example of the present disclosure.

FIG. 9 is a flowchart of a method of determining the presence of phrenic nerve stimulation in a medical device, according to an example of the present disclosure. As illustrated in FIGS. 8 and 9, during detection of phrenic nerve stimulation in an example in which the PNS test signal is a heart sounds signal and the predetermined cardiac signal is a Vp beat, the device senses the heart sounds signal 318 and determines heart sounds processing windows of the heart sounds signal 318 for a current beat, Block 340. For example, the device determines the heart sounds based PNS window, i.e., PreVp window 322 and post Vp window 326, for the current sensed Vp beat. Signal artifacts of the heart sounds signal, such as one or more of a maximum, a minimum, a range, a mean, a sum and an absolute difference are calculated within the heart sounds based PNS window. i.e., PreVp window 322 and PostVp window 326. Absolute difference is analogous to standard deviation (SD) and is calculated by subtracting the mean from a signal, summing the absolute value of the resulting time series and dividing by the length of the signal. Using the determined heart sounds signal artifacts, the device determines whether PNS beat criteria are met for the beat. If the PNS beat criteria are met, the beat is determined to be a PNS beat. On the other hand, if the PNS beat criteria are not met, the beat is not determined to be a PNS beat.

In order to determine whether the PNS beat criteria are met, the device determines whether a maximum of the absolute value of the filtered heart sounds signal |FHS| within the postVp window 326 criteria and a sum of the absolute value of the filtered heart sounds signal |FHS| within the postVp window 326 criteria are satisfied. For example, the device may determine whether the maximum of the absolute value of the filtered heart sounds signal |FHS| within the postVp window 326 is greater than a PNS maximum threshold, Block 342.

In one example, the PNS maximum threshold in Block 342 of FIG. 9 may be set as the sum of 3 times the mean of the absolute value of the filtered heart sounds signal |FHS| within the PreVp window 322 and two times the standard deviation, i.e., the absolute difference, of the filtered heart sounds signal |FHS| within the PreVp window 322.

In another example, the PNS maximum threshold in Block 342 may be set as a variable PNS maximum threshold, α. For example, as illustrated below in Table 1, the variable PNS maximum threshold α may be a function of the range of the filtered heart sounds signal FHS in the noise window 328. For example, as shown in Table 1, the variable PNS maximum threshold α may be set as 80 ADC units if the range of the filtered heart sounds signal FHS is less than 1070 ADC units, may be set as 500 ADC units if the range of the filtered heart sounds signal FHS is between 1070 ADC units and 7000 ADC units, and may be set as 1800 ADC units if the range of the filtered heart sounds signal FHS is greater than or equal to 7000 ADC units.

TABLE 1

| Range of FHS | α | β |
|---|---|---|
| <1070 | 80 | 250 |
| 1070 to <7000 | 350 | 1000 |
| ≥7000 | 1800 | 400 |

In another example, the device may determine that the maximum of the absolute value of the filtered heart sounds signal |FHS| within the postVp window 326 is greater than the PNS maximum threshold, Yes in Block 342, if the absolute value of the filtered heart sounds signal |FHS| within the PostVp window 326 is determined both to be greater than the sum of 3 times the mean of the absolute value of the filtered heart sounds signal |FHS| within the PreVp window 322 and two times the standard deviation of the filtered heart sounds signal |FHS| within the PreVp window 322, and greater than the variable PNS maximum threshold, α.

If the maximum of the absolute value of the filtered heart sounds signal |FHS| within the postVp window 326 is greater than the PNS maximum sum threshold, YES in Block 342, the device determines whether the sum of the absolute value of the filtered heart sounds signal |FHS| within the postVp window 326 is greater than a PNS sum threshold, Block 344. If the sum of the absolute value of the filtered heart sounds signal |FHS| within the postVp window 326 is greater than the variable PNS sum threshold, YES in Block 344, the current beat is determined to be a PNS beat, Block 346. On the other hand, if either the maximum of the absolute value of the filtered heart sounds signal |FHS| within the postVp window 326 is not greater than the PNS maximum sum threshold, No in Block 342, or the sum of the absolute value of the filtered heart sounds signal |FHS| within the postVp window 326 is not greater than the PNS sum threshold, No in Block 344, the current Vp beat is determined not to be a PNS beat, Block 348.

In one example the PNS sum threshold of Block 344 may be a sum of the absolute value of the filtered heart sounds signal |FHS| within the PreVp window 322 and a PNS beat sum variable threshold, β. For example, as illustrated in Table 1, the variable PNS sum threshold β may be a function of the range of the filtered heart sounds signal FHS in the noise window 328. For example, as shown in Table 1, the variable PNS sum threshold β may be set as 250 ADC units if the range of the filtered heart sounds signal FHS is less than 1070 ADC units, may be set as 1000 ADC units if the range of the filtered heart sounds signal FHS is between 1070 ADC units and 7000 ADC units, and may be set as 400 ADC units if the range of the filtered heart sounds signal FHS is greater than or equal to 7000 ADC units.

In another example, the PNS sum threshold of Block 344 may be a multiple of the sum of the absolute value of the filtered heart sounds signal |FHS| within the PreVp window 322, such as 1.25 times the sum of absolute value of the filtered heart sounds signal |FHS| within the PreVp window 322, for example. In one example, the device may determine that the sum of the absolute value of the filtered heart sounds signal |FHS| within the PostVp window 326 is greater than the PNS sum threshold, Yes in Block 344, if the absolute value of the filtered heart sounds signal |FHS| within the PostVp window 326 is determined to be both greater than the sum of the absolute value of the filtered heart sounds signal |FHS| within the PreVp window 322 and the variable PNS sum threshold β, and greater than the multiple of the sum of the absolute value of the filtered heart sounds signal |FHS| within the PreVp window 322, i.e., 1.25 times the sum of the absolute value of the filtered heart sounds signal |FHS| within the PreVp window 322, for example.

Each time the current beat is identified as being a PNS beat, Block 346, the device determines whether PNS episode criteria have been satisfied, Block 352. If either the PNS episode criteria have not been satisfied, NO in Block 352, or the current Vp beat is determined not to be a PNS beat, Block 348, the process continues with the next beat, Block 350, so that once the determination of the whether a current beat 320 is a PNS beat has been completed, the process is repeated for the next beat 330 until a predetermined number of beats have been evaluated for the presence of PNS. In one example, in order to ensure that the PNS evaluation is completed in less than 3 minutes at an estimated heart rate of 60 bpm for 16 vectors (11×16×1000 ms cycle length=176 s), up to 11 beats may be evaluated for PNS at the user selectable voltage output. Therefore, the device may suspend determining of a PHS episode in response to the PNS criteria having been determined for 11 consecutive beats without a PNS episode being detected.

If the PNS episode criteria have been satisfied, YES in Block 352, a PNS episode is detected, Block 354. In one example, the PNS episode criteria are determined to be satisfied, YES in Block 352, if a predetermined number of consecutive beats, such as three consecutive beats for example, are identified, on a beat-by-beat basis, as PNS beats, and therefore a PNS episode is detected, Block 354. In another example, the PNS episode criteria are determined to be satisfied, YES in Block 352, and therefore a PNS episode is detected, Block 354, if every predetermined sequential beat is determined to be a PNS beat for a total number of beats, such as every third beat for three total beats, i.e., beat(i), beat (i−3), beat (i−6), for example, is determined to be a PNS beat. Once a PNS episode is detected, Block 354, the device may store the determination that a PNS episode was detected, generate an alert, adjust the pacing vector for delivery of the pacing therapy, or suspend delivery of the pacing therapy.

Figure 10:
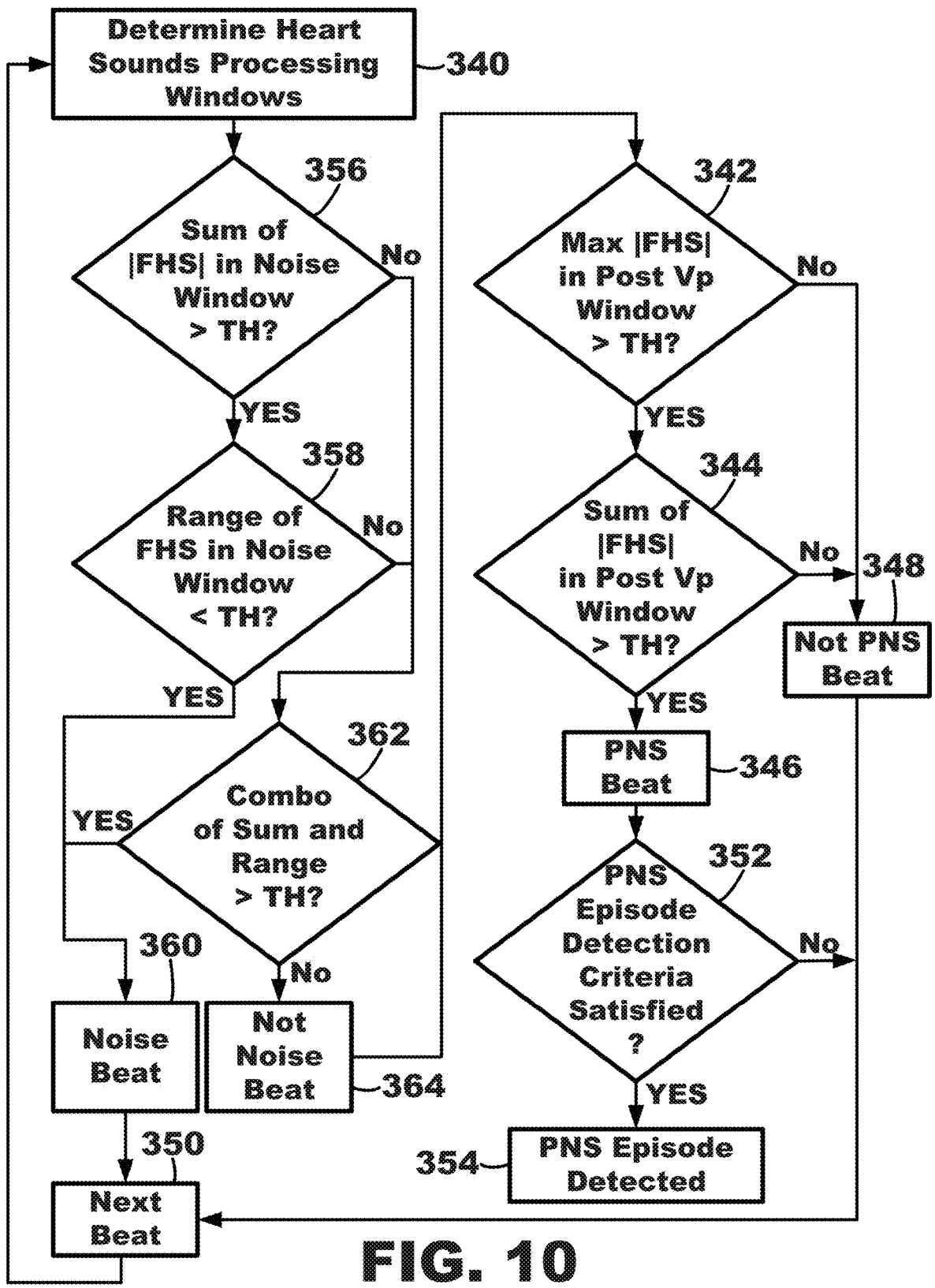
FIG. 10 is a flowchart of a method of determining the presence of phrenic nerve stimulation in a medical device, according to an example of the present disclosure.

FIG. 10 is a flowchart of a method of determining the presence of phrenic nerve stimulation in a medical device, according to an example of the present disclosure. In certain instances, it may be desirable to ensure that the determination of a beat being a PNS beat does not occur as a result of noise occurring in the test signal. For example, as illustrated in FIGS. 8 and 10, during detection of phrenic nerve stimulation, the device senses the heart sounds signal 318 and in determining heart sounds processing windows of the heart sounds signal 318 for a current beat, Block 340, determines a heart sounds based noise window in addition to determining the heart sounds based PNS window, i.e., PreVp window 322 and PostVp window 326, described above. As a result, signal features of the heart sounds signal, such as one or more of a maximum, a minimum, a range, a mean, a sum and an absolute difference are calculated within each of the heart sounds based noise window 328 and the heart sounds based PNS window. i.e., PreVp window 322 and PostVp window 326. Absolute difference is analogous to standard deviation (SD) and is calculated by subtracting the mean from a signal, summing the absolute value of the resulting time series and dividing by the length of the signal. In the example of FIG. 10, the heart sound signal features within the noise window 328 for the beat are first evaluated to detect or determine whether the beat is associated with noise. If noise is not detected for the beat, the heart sound signal features within PreVp window 322 and PostVp window 326 for the beat are then evaluated to detect or determine whether the beat is associated with the presence of PNS.

As illustrated in the example of FIG. 10, during the evaluation of the noise window 328, the device determines whether a sum of the absolute value of the filtered heart sounds signal |FHS| within the noise window 328 is greater than a noise sum threshold, Block 356. If the sum of the absolute value of the filtered heart sounds signal |FHS| within the noise window 328 is greater than the noise sum threshold, YES in Block 356, the device determines whether a range (i.e., the difference between the maximum and the minimum) of the filtered heart sounds signal FHS in the noise window 328 is less than a noise range threshold, Block 358. If the range of the filtered heart sounds signal FHS in the noise window 328 is less than the noise range threshold, YES in Block 358, the current beat is identified as a noise beat, Block 360, and the process continues with the next beat, Block 350.

If either the sum of the absolute value of the filtered heart sounds signal |FHS| within the noise window 328 is not greater than the noise sum threshold, NO in Block 356, or the range of the filtered heart sounds signal FHS in the noise window 328 is not less than the noise range threshold, NO in Block 358, the device determines whether a combination of the sum of the absolute value of the filtered heart sounds signal |FHS| and the range of the filtered heart sounds signal FHS in the noise window 328 is greater than a combination threshold, Block 362. In one example, in order to determine whether the combination is greater than the combination threshold in Block 362, the device determines whether a product of the sum of the absolute value of the filtered heart sounds signal |FHS| and the range of the filtered heart sounds signal FHS in the noise window 328 is greater than the combination threshold.

If the sum of the absolute value of the filtered heart sounds signal |FHS| and the range of the filtered heart sounds signal FHS in the noise window 328 is greater than the combination threshold, YES in Block 362, the current beat is identified as a noise beat, Block 360, and the process continues with the next beat, Block 350. On the other hand, if sum of the absolute value of the filtered heart sounds signal |FHS| and the range of the filtered heart sounds signal FHS in the noise window 328 is not greater than the combination threshold, NO in Block 362, the current beat is identified as not being a noise beat, Block 364. According to one example, the noise sum threshold may be set as 22900 ADC units, the noise range threshold may be set as 1000 ADC units, and the combination threshold may be set as 170000000 ADC units squared if the combination is a product of the two thresholds.

In this way, a noise beat criteria for the current beat is met, and the beat is determined to be a noise beat, Block 360, if both the sum of the absolute value of the filtered heart sounds signal |FHS| within the noise window 328 is greater than the noise sum threshold, YES in Block 356, and the range of the filtered heart sounds signal FHS in the noise window 328 is less than the noise range threshold, YES in Block 358, or if the product of the sum of the absolute value of the filtered heart sounds signal |FHS| and the range of the filtered heart sounds signal FHS in the noise window 328 is greater than the combination threshold, YES in Block 362. On the other hand, the noise beat criteria for the current beat are not met, and the beat is not determined to be a noise beat, Block 364, if either the sum of the absolute value of the filtered heart sounds signal |FHS| within the noise window 328 is not greater than the noise sum threshold, NO in Block 356, or the range of the filtered heart sounds signal FHS in the noise window 328 is not less than the noise range threshold, NO in Block 358, and the product of the sum of the absolute value of the filtered heart sounds signal |FHS| and the range of the filtered heart sounds signal FHS in the noise window 328 is not greater than the combination threshold, NO in Block 362.

When the noise beat criteria, Blocks 356, 358 and 362, for the current beat are not satisfied, and therefore the current beat is not determined to be a noise beat, Block 364, the device determines whether PNS beat criteria are met for the beat, using the method for such determination as described above in FIG. 9, and the determination is not repeated here for brevity sake. Each time the current beat is identified as being a PNS beat, Block 346, the device determines whether PNS episode criteria have been satisfied, Block 352. If either the PNS episode criteria have not been satisfied, NO in Block 352, or the current Vp beat is determined not to be a PNS beat, Block 348, the process continues with the next beat, Block 350, so that once the determination of the whether a current beat 320 is a PNS beat has been completed, the process is repeated for the next beat 330 until a predetermined number of beats have been evaluated for the presence of PNS. In one example, in order to ensure that the PNS evaluation is completed in less than 3 minutes at an estimated heart rate of 60 bpm for 16 vectors (11×16×1000 ms cycle length=176 s), up to 11 beats may be evaluated for PNS at the user selectable voltage output. Therefore, the device may suspend determining of a PHS episode in response to the PNS criteria having been determined for 11 consecutive beats without a PNS episode being detected.

If the PNS episode criteria have been satisfied, YES in Block 352, a PNS episode is detected, Block 354. In one example, the PNS episode criteria are determined to be satisfied, YES in Block 352, if a predetermined number of consecutive beats, such as three consecutive beats for example, are identified, on a beat-by-beat basis, as PNS beats, and therefore a PNS episode is detected, Block 354. In another example, the PNS episode criteria are determined to be satisfied, YES in Block 352, and therefore a PNS episode is detected, Block 354, if every predetermined sequential beat is determined to be a PNS beat for a total number of beats, such as every third beat for three total beats, i.e., beat(i), beat (i−3), beat (i−6), for example, is determined to be a PNS beat. Once a PNS episode is detected, Block 354, the device may store the determination that a PNS episode was detected, generate an alert, adjust the pacing vector for delivery of the pacing therapy, or suspend delivery of the pacing therapy.

PNS beat criteria and noise beat criteria for determining phrenic nerve stimulation in a medical device according to one example of the present disclosure may be as summarized below:

Noise beat criteria=(A AND B) OR C
A: Sum of |FHS| in noise window >22900
B: Range of FHS in noise window <1000
C: A×B>170000000
PNS beat criteria=D AND E AND F AND G
D: Max of |FHS| in PostVp>3×Mean of |FHS| in PreVp+ 2×SD of |FHS| in PreVp
E: Max of |FHS| in PostVp>α
F: Sum of |FHS| in PostVp>Sum of |FHS| in PreVp+β
G: Sum of |FHS| in PostVp>1.25×Sum of |FHS| in PreVp In the example illustrated in FIG. 9, the device determines acoustic artifacts of the sensed heart sounds signal within the pre-ventricular paced (PreVP) window 322 and the post-ventricular (PostVP) window 326 of the heart sounds signal sensed during a ventricular paced beat 320 delivered by the device. The device determines, in response to acoustic artifacts of the sensed heart sounds signal within the pre-ventricular paced (PreVP) window and the post-ventricular (PostVP) window, whether PNS criteria have been satisfied. In response to the PNS criteria being satisfied, the device determines whether PNS episode criteria have been satisfied, and detects a PNS episode in response to the PNS episode criteria being satisfied. It is understood that while any combination of PNS beat criteria D-G may be utilized to determine whether PNS beat criteria have been satisfied, in one example the device may identify the current beat as a PNS beat if the maximum of the |FHS| within the PostVp window is determined to be greater than the sum of 3 times the mean of the |FHS| within the PreVp window and two times the standard deviation of the |FHS| within the PreVp window (PNS Beat Criteria D), the maximum of the |FHS| within the PostVp window is determined to be greater than a variable PNS maximum threshold α (PNS Beat Criteria E), wherein the variable PNS maximum threshold is a function of a range of the filtered heart sounds signal (FHS) in the noise window, the sum of the |FHS| within the PostVp window is determined to be greater than a sum of the |FHS| within the PreVp window and a variable PNS sum threshold β (PNS Beat Criteria F), wherein the variable PNS beat sum threshold is a function of the range of the filtered heart sounds signal FHS in the noise window, and the sum of the |FHS| within the PostVp window is determined to be greater than a multiple of the sum of the |FHS| within the PreVp window (PNS Beat Criteria F).

In the example illustrated in FIG. 10, the device determines acoustic artifacts within each of the noise window 328, the pre-ventricular paced (PreVP) window 322 and the post-ventricular (PostVP) window 326 of the heart sounds signal sensed during a ventricular paced beat 320 delivered by the device. The device determines, in response to acoustic artifacts of the sensed heart sounds signal within the noise window, whether noise criteria have been satisfied, and determines, in response to acoustic artifacts of the sensed heart sounds signal within the pre-ventricular paced (PreVP) window and the post-ventricular (PostVP) window, whether PNS criteria have been satisfied. In response to the PNS criteria being satisfied, the device determines whether PNS episode criteria have been satisfied, and detects a PNS episode in response to the PNS episode criteria being satisfied.

It is understood that while any combination of PNS Noise Beat Criteria A-C may be utilized to determine whether PNS noise criteria have been satisfied, in one example the device may identify the current beat as a noise beat in response to both the sum of the |FHS| within the noise window being greater than the noise sum threshold (PNS Noise Beat Criteria A) and the range of the FHS within the noise window being less than the noise range threshold (PNS Noise Beat Criteria B), or in response to a product of the sum of the |FHS| in the noise window and the range of the FHS in the noise window being greater than a combination threshold (PNS Noise Beat Criteria C). In addition, the device identifies the current beat as not being a noise beat in response to at least one of the sum of the |FHS| within the noise window not being greater than the noise sum threshold and the range of the FHS within the noise window not being less than the noise range threshold, and a product of the sum of the |FHS| in the noise window and the range of the FHS in the noise window not being greater than a combination threshold.

Techniques for detecting stimulation of one or more of phrenic nerves 36 and 38 are primarily described herein as being performed by IMD 16, e.g., by a processor of IMD 16. In other examples, some or all of the functions ascribed to IMD 16 or a processor thereof may be performed by one or more other devices such as programmer 24, or a processor thereof. For example, IMD 16 may process cardiac and/or heart sound signals to determine whether therapy should continue to be delivered based on current parameters, or whether adjustments to the parameters should be made, and control the parameters used by IMD 16 to deliver the therapy. Alternatively, programmer 24 may process cardiac and/or heart sound signals received from IMD 16 to determine whether therapy should continue to be delivered based on current parameters or whether adjustments to the parameters should be made, and control according to what parameters IMD 16 delivers the therapy. Furthermore, although described herein with respect to an IMD, in other examples, the techniques described herein may be performed or implemented in an external medical device, which may be coupled to a patient via percutaneous or transcutaneous leads. In some examples, various functions of IMD 16 may be carried out by multiple IMDs in communication with one another.

ILLUSTRATIVE EMBODIMENTS

Embodiment 1: A method of detecting phrenic nerve stimulation (PNS) in a cardiac medical device, comprising:
sensing a test signal, the test signal being sensitive to contraction of a diaphragm of a patient;
determining signal artifacts of the test signal within each of a first window of the test signal prior to a predetermined cardiac signal and a second window of the test signal subsequent to the predetermined cardiac signal;
determining, in response to signal artifacts of the test signal within the first window and the second window, whether PNS beat criteria have been satisfied;
determining, in response to the PNS beat criteria being satisfied, whether PNS episode criteria have been satisfied; and
detecting a PNS episode in response to the PNS episode criteria being satisfied.

Embodiment 2: The method of embodiment 1, wherein the test signal comprises one of an acoustic signal and an accelerometer signal.

Embodiment 3: The method as in any one of embodiments 1-2, wherein the predetermined cardiac signal comprises at least one of a ventricular pace (Vp) beat, an atrial sense (As) beat, and an atrial pace (Ap) beat.

Embodiment 4: The method as in any one of embodiments 1-3, wherein the test signal comprises a heart sounds signal, and wherein determining whether PNS beat criteria have been satisfied comprises:
determining whether a maximum of the absolute value of the heart sounds signal (|FHS|) within the second window is satisfied;
determining whether a sum of the |FHS| within the second window is satisfied; and
determining PNS criteria have been satisfied in response to both the maximum of the |FHS| within the second window and the sum of the |FHS| within the second window being satisfied.

Embodiment 5: The method of embodiment 4, further comprising determining signal artifacts of the test signal within a third window of the test signal subsequent to the predetermined cardiac signal and different from the second window, wherein determining whether the maximum of the |FHS| within the second window is satisfied comprises:
  determining whether the maximum of the |FHS| within the second window is greater than the sum of 3 times the mean of the |FHS| within the first window and two times the standard deviation of the |FHS| within the first window; and
  determining whether the maximum of the |FHS| within the second window is greater than a variable PNS maximum threshold, wherein the variable PNS maximum threshold is a function of a range of the heart sounds signal (FHS) in the third window.

Embodiment 6: The method of embodiment 5, wherein determining whether the sum of the |FHS| within the second window is satisfied comprises:
  determining whether the sum of the |FHS| within the second window is greater than a sum of the |FHS| within the first window and a variable PNS sum threshold, wherein the variable PNS beat sum threshold is a function of the range of the heart sounds signal FHS in the third window; and
  determining whether the sum of the |FHS| within the second window is greater than a multiple of the sum of the |FHS| within the first window.

Embodiment 7: The method as in any one of embodiments 1-6, further comprising:
  determining signal artifacts of the test signal within a third window of the test signal subsequent to the predetermined cardiac signal and different from the second window; and
  determining, in response to signal artifacts of the test signal within the third window, whether noise criteria have been satisfied.

Embodiment 8: The method of embodiment 7, wherein determining whether noise criteria have been satisfied comprises:
  determining whether a sum of the absolute value of the heart sounds signal (|FHS|) within the third window is greater than a noise sum threshold;
  determining whether a range of the heart sounds signal (FHS) within the third window is less than a noise range threshold; and
  identifying the beat as a noise beat in response to both the sum of the |FHS| within the third window being greater than the noise sum threshold and the range of the FHS within the third window being less than the noise range threshold.

Embodiment 9: The method of embodiment 8, further comprising:
  determining, in response to at least one of the sum of the |FHS| within the third window not being greater than the noise sum threshold and the range of the FHS within the third window not being less than the noise range threshold, whether a product of the sum of the |FHS| in the third window and the range of the FHS in the third window is greater than a combination threshold; and
  identifying the predetermined cardiac signal as not being a noise beat in response to the product of the sum of the |FHS| and the range of the FHS in the third window not being greater than the combination threshold.

Embodiment 10: The method as in any one of embodiments 1-8, wherein determining whether PNS episode criteria have been satisfied comprises one of:
  determining whether the PNS criteria are satisfied for a predetermined number of consecutive beats, and
  determining whether the PNS criteria are satisfied for each predetermined sequential beat over a number of beats.

Embodiment 11: The method as in any one of embodiments 1-10, further comprising performing, in response to the PNS episode being detected, one of:
  storing the determination that the PNS episode was detected,
  generating an alert,
  adjusting a pacing vector, and
  suspending delivery of a pacing therapy.

Embodiment 12: A cardiac medical device, comprising:
  a first sensor to sense a test signal, the test signal being sensitive to contraction of a diaphragm of a patient;
  a second sensor to sense a predetermined cardiac signal; and
  a processor operably coupled to the first sensor and the second sensor and configured to:
    determine signal artifacts of the test signal within each of a first window of the test signal prior to a predetermined cardiac signal and a second window of the test signal subsequent to the predetermined cardiac signal,
    determine, in response to signal artifacts of the test signal within the first window and the second window, whether PNS beat criteria have been satisfied,
    determine, in response to the PNS beat criteria being satisfied, whether PNS episode criteria have been satisfied, and
    detect a PNS episode in response to the PNS episode criteria being satisfied.

Embodiment 13: The device of embodiment 12, wherein the test signal comprises one of an acoustic signal and an accelerometer signal.

Embodiment 14: The device as in any one of embodiments 12-13, wherein the predetermined cardiac signal comprises at least one of a ventricular pace (Vp) beat, an atrial sense (As) beat, and an atrial pace (Ap) beat.

Embodiment 15: The device as in any one of embodiments 12-14, wherein the test signal comprises a heart sounds signal, wherein, to determine whether PNS beat criteria have been satisfied, the processor is further configured to:
  determine whether a maximum of the absolute value of the heart sounds signal (|FHS|) within the second window is satisfied, determine whether a sum of the |FHS| within the second window is satisfied, and
  determine PNS criteria have been satisfied in response to both the maximum of the |FHS| within the second window and the sum of the |FHS| within the second window being satisfied.

Embodiment 16: The device of embodiment 15, wherein the processor is further configured to:
  determine signal artifacts of the test signal within a third window of the test signal subsequent to the predetermined cardiac signal and different from the second window,
  determine whether the maximum of the |FHS| within the second window is greater than the sum of 3 times the mean of the |FHS| within the first window and two times the standard deviation of the |FHS| within the first window, and
  determine whether the maximum of the |FHS| within the second window is greater than a variable PNS maximum threshold, wherein the variable PNS maximum threshold is a function of a range of the heart sounds signal (FHS) in the third window.

Embodiment 17: The device of embodiment 16, wherein, to determine whether a sum of the |FHS| within the second window is satisfied, the processor is further configured to:
determine whether the sum of the |FHS| within the second window is greater than a sum of the |FHS| within the first window and a variable PNS sum threshold, wherein the variable PNS beat sum threshold is a function of the range of the heart sounds signal FHS in the third window, and
determine whether the sum of the |FHS| within the second window is greater than a multiple of the sum of the |FHS| within the first window.

Embodiment 18: The device as in any one of embodiments 12-17, wherein the processor is further configured to:
determine signal artifacts of the test signal within a third window of the test signal subsequent to the predetermined cardiac signal and different from the second window, and
determine, in response to signal artifacts of the test signal within the third window, whether noise criteria have been satisfied.

Embodiment 19: The device of embodiment 18, wherein, to determine whether noise criteria have been satisfied, the processor is further configured to:
determine whether a sum of the absolute value of the heart sounds signal (|FHS|) within the third window is greater than a noise sum threshold,
determine whether a range of the heart sounds signal (FHS) within the third window is less than a noise range threshold, and
identify the predetermined cardiac signal as a noise beat in response to both the sum of the |FHS| within the third window being greater than the noise sum threshold and the range of the FHS within the third window being less than the noise range threshold.

Embodiment 20: The device of embodiment 19, wherein the processor is further configured to:
determine, in response to at least one of the sum of the |FHS| within the third window not being greater than the noise sum threshold and the range of the FHS within the third window not being less than the noise range threshold, whether a product of the sum of the |FHS| in the third window and the range of the FHS in the third window is greater than a combination threshold, and
identify the predetermined cardiac signal as not being a noise beat in response to the product of the sum of the |FHS| and the range of the FHS in the third window not being greater than the combination threshold.

Embodiment 21: The device as in any one of embodiments 12-20, wherein the processor is further configured to determine one of:
whether the PNS criteria are satisfied for a predetermined number of consecutive beats, and
whether the PNS criteria are satisfied for each predetermined sequential beat over a number of beats.

Embodiment 22: The device as in any one of embodiments 12-21, wherein the processor is configured to perform one of:
storing the determination that the PNS episode was detected,
generating an alert,
adjusting a pacing vector, and
suspending delivery of a pacing therapy by the device in response to a PNS episode being detected.

Embodiment 23: A non-transitory computer readable medium storing instructions which cause a cardiac medical device to perform a method comprising:
sensing a test signal, the test signal being sensitive to contraction of a diaphragm of a patient;
determining signal artifacts of the test signal within each of a first window of the test signal prior to a predetermined cardiac signal and a second window of the test signal subsequent to the predetermined cardiac signal;
determining, in response to signal artifacts of the test signal within the first window and the second window, whether PNS beat criteria have been satisfied;
determining, in response to the PNS beat criteria being satisfied, whether PNS episode criteria have been satisfied; and
detecting a PNS episode in response to the PNS episode criteria being satisfied.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed:

1. A method of detecting phrenic nerve stimulation (PNS) in a cardiac medical device, comprising:
sensing a test signal, the test signal being sensitive to contraction of a diaphragm of a patient;
determining signal artifacts of the test signal within each of a first window of the test signal prior to a predetermined cardiac signal and a second window of the test signal subsequent to the predetermined cardiac signal;
determining, in response to signal artifacts of the test signal within the first window and the second window, whether PNS beat criteria have been satisfied;
determining, in response to the PNS beat criteria being satisfied, whether PNS episode criteria have been satisfied; and
detecting a PNS episode in response to the PNS episode criteria being satisfied.

2. The method of claim 1, wherein the test signal comprises one of an acoustic signal and an accelerometer signal.

3. The method of claim 1, wherein the predetermined cardiac signal comprises at least one of a ventricular pace (Vp) beat, an atrial sense (As) beat, and an atrial pace (Ap) beat.

4. The method of claim 1, wherein the test signal comprises a heart sounds signal, and wherein determining whether PNS beat criteria have been satisfied comprises:
determining whether a maximum of the absolute value of the heart sounds signal (|FHS|) within the second window is satisfied;
determining whether a sum of the |FHS| within the second window is satisfied; and
determining PNS criteria have been satisfied in response to both the maximum of the |FHS| within the second window and the sum of the |FHS| within the second window being satisfied.

5. The method of claim 4, further comprising determining signal artifacts of the test signal within a third window of the test signal subsequent to the predetermined cardiac signal and different from the second window, wherein determining whether the maximum of the |FHS| within the second window is satisfied comprises:
  determining whether the maximum of the |FHS| within the second window is greater than the sum of 3 times the mean of the |FHS| within the first window and two times the standard deviation of the |FHS| within the first window; and
  determining whether the maximum of the |FHS| within the second window is greater than a variable PNS maximum threshold, wherein the variable PNS maximum threshold is a function of a range of the heart sounds signal (FHS) in the third window.

6. The method of claim 5, wherein determining whether the sum of the |FHS| within the second window is satisfied comprises:
  determining whether the sum of the |FHS| within the second window is greater than a sum of the |FHS| within the first window and a variable PNS sum threshold, wherein the variable PNS beat sum threshold is a function of the range of the heart sounds signal FHS in the third window; and
  determining whether the sum of the |FHS| within the second window is greater than a multiple of the sum of the |FHS| within the first window.

7. The method of claim 1, further comprising:
  determining signal artifacts of the test signal within a third window of the test signal subsequent to the predetermined cardiac signal and different from the second window; and
  determining, in response to signal artifacts of the test signal within the third window, whether noise criteria have been satisfied.

8. The method of claim 7, wherein determining whether noise criteria have been satisfied comprises:
  determining whether a sum of the absolute value of the heart sounds signal (|FHS|) within the third window is greater than a noise sum threshold;
  determining whether a range of the heart sounds signal (FHS) within the third window is less than a noise range threshold; and
  identifying the beat as a noise beat in response to both the sum of the |FHS| within the third window being greater than the noise sum threshold and the range of the FHS within the third window being less than the noise range threshold.

9. The method of claim 8, further comprising:
  determining, in response to at least one of the sum of the |FHS| within the third window not being greater than the noise sum threshold and the range of the FHS within the third window not being less than the noise range threshold, whether a product of the sum of the |FHS| in the third window and the range of the FHS in the third window is greater than a combination threshold; and
  identifying the predetermined cardiac signal as not being a noise beat in response to the product of the sum of the |FHS| and the range of the FHS in the third window not being greater than the combination threshold.

10. The method of claim 1, wherein determining whether PNS episode criteria have been satisfied comprises one of:
  determining whether the PNS criteria are satisfied for a predetermined number of consecutive beats, and
  determining whether the PNS criteria are satisfied for each predetermined sequential beat over a number of beats.

11. The method of claim 1, further comprising performing, in response to the PNS episode being detected, one of:
  storing the determination that the PNS episode was detected,
  generating an alert,
  adjusting a pacing vector, and
  suspending delivery of a pacing therapy.

12. A cardiac medical device, comprising:
  a first sensor to sense a test signal, the test signal being sensitive to contraction of a diaphragm of a patient;
  a second sensor to sense a predetermined cardiac signal; and
  a processor operably coupled to the first sensor and the second sensor and configured to:
    determine signal artifacts of the test signal within each of a first window of the test signal prior to a predetermined cardiac signal and a second window of the test signal subsequent to the predetermined cardiac signal,
    determine, in response to signal artifacts of the test signal within the first window and the second window, whether PNS beat criteria have been satisfied,
    determine, in response to the PNS beat criteria being satisfied, whether PNS episode criteria have been satisfied, and
    detect a PNS episode in response to the PNS episode criteria being satisfied.

13. The device of claim 12, wherein the test signal comprises one of an acoustic signal and an accelerometer signal.

14. The device of claim 12, wherein the predetermined cardiac signal comprises at least one of a ventricular pace (Vp) beat, an atrial sense (As) beat, and an atrial pace (Ap) beat.

15. The device of claim 12, wherein the test signal comprises a heart sounds signal, wherein, to determine whether PNS beat criteria have been satisfied, the processor is further configured to:
  determine whether a maximum of the absolute value of the heart sounds signal (|FHS|) within the second window is satisfied,
  determine whether a sum of the |FHS| within the second window is satisfied, and
  determine PNS criteria have been satisfied in response to both the maximum of the |FHS| within the second window and the sum of the |FHS| within the second window being satisfied.

16. The device of claim 15, wherein the processor is further configured to:
  determine signal artifacts of the test signal within a third window of the test signal subsequent to the predetermined cardiac signal and different from the second window,
  determine whether the maximum of the |FHS| within the second window is greater than the sum of 3 times the mean of the |FHS| within the first window and two times the standard deviation of the |FHS| within the first window, and
  determine whether the maximum of the |FHS| within the second window is greater than a variable PNS maximum threshold, wherein the variable PNS maximum threshold is a function of a range of the heart sounds signal (FHS) in the third window.

17. The device of claim 16, wherein, to determine whether a sum of the |FHS| within the second window is satisfied, the processor is further configured to:
  determine whether the sum of the |FHS| within the second window is greater than a sum of the |FHS| within the first window and a variable PNS sum threshold, wherein the variable PNS beat sum threshold is a function of the range of the heart sounds signal FHS in the third window, and determine whether the sum of the |FHS| within the second window is greater than a multiple of the sum of the |FHS| within the first window.

18. The device of claim 12, wherein the processor is further configured to:

determine signal artifacts of the test signal within a third window of the test signal subsequent to the predetermined cardiac signal and different from the second window, and determine, in response to signal artifacts of the test signal within the third window, whether noise criteria have been satisfied.

19. The device of claim 18, wherein, to determine whether noise criteria have been satisfied, the processor is further configured to:

determine whether a sum of the absolute value of the heart sounds signal (|FHS|) within the third window is greater than a noise sum threshold, determine whether a range of the heart sounds signal (FHS) within the third window is less than a noise range threshold, and identify the predetermined cardiac signal as a noise beat in response to both the sum of the |FHS| within the third window being greater than the noise sum threshold and the range of the FHS within the third window being less than the noise range threshold.

20. The device of claim 19, wherein the processor is further configured to:

determine, in response to at least one of the sum of the |FHS| within the third window not being greater than the noise sum threshold and the range of the FHS within the third window not being less than the noise range threshold, whether a product of the sum of the |FHS| in the third window and the range of the FHS in the third window is greater than a combination threshold, and identify the predetermined cardiac signal as not being a noise beat in response to the product of the sum of the |FHS| and the range of the FHS in the third window not being greater than the combination threshold.

21. The device of claim 12, wherein the processor is further configured to determine one of:

whether the PNS criteria are satisfied for a predetermined number of consecutive beats, and whether the PNS criteria are satisfied for each predetermined sequential beat over a number of beats.

22. The device of claim 12, wherein the processor is configured to perform one of:

storing the determination that the PNS episode was detected, generating an alert, adjusting a pacing vector, and suspending delivery of a pacing therapy by the device in response to a PNS episode being detected.

23. A non-transitory computer readable medium storing instructions which cause a cardiac medical device to perform a method comprising:

sensing a test signal, the test signal being sensitive to contraction of a diaphragm of a patient;

determining signal artifacts of the test signal within each of a first window of the test signal prior to a predetermined cardiac signal and a second window of the test signal subsequent to the predetermined cardiac signal;

determining, in response to signal artifacts of the test signal within the first window and the second window, whether PNS beat criteria have been satisfied;

determining, in response to the PNS beat criteria being satisfied, whether PNS episode criteria have been satisfied; and detecting a PNS episode in response to the PNS episode criteria being satisfied.

* * * * *